US012678051B2

(12) United States Patent
Jacquel et al.

(10) Patent No.: US 12,678,051 B2
(45) Date of Patent: * Jul. 14, 2026

(54) VIDEO-BASED PATIENT MONITORING SYSTEMS AND ASSOCIATED METHODS FOR DETECTING AND MONITORING BREATHING

(71) Applicant: Covidien LP, Mansfield, MA (US)

(72) Inventors: Dominique Jacquel, Edinburgh (GB);
Paul S. Addison, Edinburgh (GB);
David Ming Hui Foo, Glasgow (GB)

(73) Assignee: Covidien LP, Mansfield, MA (US)

( * ) Notice: Subject to any disclaimer, the term of this patent is extended or adjusted under 35 U.S.C. 154(b) by 93 days.

This patent is subject to a terminal disclaimer.

(21) Appl. No.: 18/742,318

(22) Filed: Jun. 13, 2024

(65) Prior Publication Data

US 2024/0324883 A1 Oct. 3, 2024

Related U.S. Application Data

(63) Continuation of application No. 17/656,597, filed on Mar. 25, 2022, now Pat. No. 12,016,655, which is a
(Continued)

(51) Int. Cl.
*A61B 5/00* (2006.01)
*A61B 5/08* (2006.01)
(Continued)

(52) U.S. Cl.
CPC .......... *A61B 5/0077* (2013.01); *A61B 5/0803* (2013.01); *A61B 5/0806* (2013.01);
(Continued)

(58) Field of Classification Search
USPC ........................................................ 382/128
See application file for complete search history.

(56) References Cited

U.S. PATENT DOCUMENTS 5,107,845 A 4/1992 Guern et al.
5,408,998 A 4/1995 Mersch
(Continued)

FOREIGN PATENT DOCUMENTS

CA 2234191 A1 10/1998
CN 106725410 A 5/2017
(Continued)

OTHER PUBLICATIONS

Povsic et al., Real-time 3D visualization of thoraco-abdominal surface during breathing with body movement and deformation extraction, Physiological Measurement, vol. 36, No. 7, May 28, 2015, pp. 1497-1516. (Year: 2015).*
(Continued)

*Primary Examiner* — Ishrat I Sherali
(74) *Attorney, Agent, or Firm* — Dymera IP, LLC

(57) ABSTRACT

The present disclosure relates to the field of medical monitoring, and, in particular, to non-contact detecting and monitoring of patient breathing. Systems, methods, and computer readable media are described for calculating a change in depth of regions in one or more regions of interest (ROI's) on a patient and assigning one or more visual indicators to the regions based on the calculated changes in depth of the regions over time. In some embodiments, one or more breathing parameter signals corresponding to the regions can be generated and/or analyzed. In these and other embodiments, the one or more visual indicators can be displayed overlaid onto the regions in real-time. In these and still other embodiments, the systems, methods, and/or computer readable media (i) can display one or more generated breathing parameter signals in real-time and/or (ii) can trigger an alert and/or an alarm when a breathing abnormality is detected.

11 Claims, 12 Drawing Sheets

Related U.S. Application Data continuation of application No. 16/535,228, filed on Aug. 8, 2019, now Pat. No. 11,311,252.

(60) Provisional application No. 62/716,724, filed on Aug. 9, 2018.

(51) Int. Cl.
| | |
|---|---|
| *A61B 5/1171* | (2016.01) |
| *A61B 5/1455* | (2006.01) |
| *G06T 7/55* | (2017.01) |
| *H04N 13/204* | (2018.01) |

(52) U.S. Cl.
CPC .......... *A61B 5/0816* (2013.01); *A61B 5/0823* (2013.01); *A61B 5/1176* (2013.01); *A61B 5/14552* (2013.01); *A61B 5/743* (2013.01); *A61B 5/746* (2013.01); *G06T 7/55* (2017.01); *H04N 13/204* (2018.05); *G06T 2207/10028* (2013.01); *G06T 2207/30004* (2013.01)

(56) References Cited

U.S. PATENT DOCUMENTS

| | | | |
|---|---|---|---|
| 5,704,367 | A | 1/1998 | Ishikawa et al. |
| 5,800,360 | A | 9/1998 | Kisner et al. |
| 5,995,856 | A | 11/1999 | Mannheimer et al. |
| 6,241,684 | B1 | 6/2001 | Amano et al. |
| 6,668,071 | B1 | 12/2003 | Minkin et al. |
| 6,920,236 | B2 | 7/2005 | Prokoski |
| 7,431,700 | B2 | 10/2008 | Aoki et al. |
| 7,558,618 | B1 | 7/2009 | Williams |
| 8,149,273 | B2 | 4/2012 | Liu et al. |
| 8,754,772 | B2 | 6/2014 | Horng et al. |
| 8,792,969 | B2 | 7/2014 | Bernal et al. |
| 8,971,985 | B2 | 3/2015 | Bernal et al. |
| 9,226,691 | B2 | 1/2016 | Bernal et al. |
| 9,282,725 | B2 | 3/2016 | Jensen-Jarolim et al. |
| 9,301,710 | B2 | 4/2016 | Mestha et al. |
| 9,402,601 | B1 | 8/2016 | Berger et al. |
| 9,436,984 | B2 | 9/2016 | Xu et al. |
| 9,443,289 | B2 | 9/2016 | Xu et al. |
| 9,504,426 | B2 | 11/2016 | Kyal et al. |
| 9,508,141 | B2 | 11/2016 | Khachaturian et al. |
| 9,607,138 | B1 | 3/2017 | Baldwin et al. |
| 9,662,022 | B2 | 5/2017 | Kyal et al. |
| 9,693,693 | B2 | 7/2017 | Farag et al. |
| 9,693,710 | B2 | 7/2017 | Mestha et al. |
| 9,697,599 | B2 | 7/2017 | Prasad et al. |
| 9,750,461 | B1 | 9/2017 | Telfort |
| 9,839,756 | B2 | 12/2017 | Klasek |
| 9,943,371 | B2 | 4/2018 | Bresch et al. |
| 10,213,540 | B2 | 2/2019 | Burbank et al. |
| 10,219,739 | B2 * | 3/2019 | Mestha .................. A61B 5/742 |
| 10,278,585 | B2 | 5/2019 | Ferguson et al. |
| 10,376,147 | B2 | 8/2019 | Wood et al. |
| 10,398,353 | B2 | 9/2019 | Addison et al. |
| 10,447,972 | B2 | 10/2019 | Patil |
| 10,489,912 | B1 | 11/2019 | Brailovskiy |
| 10,523,852 | B2 | 12/2019 | Tzvieli et al. |
| 10,588,779 | B2 | 3/2020 | Vorhees et al. |
| 10,589,916 | B2 | 3/2020 | McRae |
| 10,650,585 | B2 | 5/2020 | Kiely |
| 10,667,723 | B2 | 6/2020 | Jacquel et al. |
| 10,702,188 | B2 | 7/2020 | Addison et al. |
| 10,729,357 | B2 | 8/2020 | Larson et al. |
| 10,874,331 | B2 | 12/2020 | Kaiser et al. |
| 10,937,296 | B1 | 3/2021 | Kukreja et al. |
| 10,939,824 | B2 | 3/2021 | Addison et al. |
| 10,939,834 | B2 | 3/2021 | Khwaja et al. |
| 10,966,059 | B1 | 3/2021 | Dayal et al. |
| 11,311,252 | B2 * | 4/2022 | Jacquel ................ A61B 5/1176 |
| 11,315,275 | B2 | 4/2022 | Addison et al. |
| 11,317,828 | B2 | 5/2022 | Addison et al. |
| 11,350,850 | B2 | 6/2022 | Jacquel et al. |
| 11,484,208 | B2 | 11/2022 | Addison |
| 11,510,584 | B2 | 11/2022 | Addison et al. |
| 11,547,313 | B2 | 1/2023 | Addison et al. |
| 11,617,520 | B2 | 4/2023 | Addison et al. |
| 11,684,287 | B2 | 6/2023 | Addison et al. |
| 11,712,176 | B2 | 8/2023 | Addison et al. |
| 11,776,146 | B2 | 10/2023 | Addison et al. |
| 11,850,026 | B2 | 12/2023 | Levi et al. |
| 11,937,900 | B2 | 3/2024 | Addison et al. |
| 12,016,655 | B2 * | 6/2024 | Jacquel ................ A61B 5/1135 |
| 2002/0137464 | A1 | 9/2002 | Dolgonos et al. |
| 2004/0001633 | A1 | 1/2004 | Caviedes |
| 2004/0258285 | A1 | 12/2004 | Hansen et al. |
| 2005/0203348 | A1 | 9/2005 | Shihadeh et al. |
| 2007/0116328 | A1 | 5/2007 | Sablak et al. |
| 2008/0001735 | A1 | 1/2008 | Tran |
| 2008/0108880 | A1 | 5/2008 | Young et al. |
| 2008/0279420 | A1 | 11/2008 | Masticola et al. |
| 2008/0295837 | A1 | 12/2008 | McCormick et al. |
| 2009/0024012 | A1 | 1/2009 | Li et al. |
| 2009/0141124 | A1 | 6/2009 | Liu et al. |
| 2009/0304280 | A1 | 12/2009 | Aharoni et al. |
| 2010/0210924 | A1 | 8/2010 | Parthasarathy et al. |
| 2010/0236553 | A1 | 9/2010 | Jafari et al. |
| 2010/0249630 | A1 | 9/2010 | Droitcour et al. |
| 2010/0324437 | A1 | 12/2010 | Freeman et al. |
| 2011/0144517 | A1 | 6/2011 | Cervantes |
| 2011/0150274 | A1 | 6/2011 | Patwardhan et al. |
| 2012/0065533 | A1 | 3/2012 | Carrillo et al. |
| 2012/0075464 | A1 | 3/2012 | Derenne et al. |
| 2012/0195473 | A1 | 8/2012 | De Haan et al. |
| 2012/0243797 | A1 | 9/2012 | Di Venuto Dayer et al. |
| 2013/0073312 | A1 | 3/2013 | Thompson et al. |
| 2013/0267873 | A1 | 10/2013 | Fuchs |
| 2013/0271591 | A1 | 10/2013 | Van Leest et al. |
| 2013/0272393 | A1 | 10/2013 | Kirenko et al. |
| 2013/0275873 | A1 | 10/2013 | Shaw et al. |
| 2013/0324830 | A1 | 12/2013 | Bernal et al. |
| 2013/0324876 | A1 | 12/2013 | Bernal et al. |
| 2014/0023235 | A1 | 1/2014 | Cennini et al. |
| 2014/0052006 | A1 | 2/2014 | Lee et al. |
| 2014/0053840 | A1 | 2/2014 | Liu |
| 2014/0073860 | A1 | 3/2014 | Urtti |
| 2014/0139405 | A1 | 5/2014 | Ribble et al. |
| 2014/0140592 | A1 | 5/2014 | Lasenby et al. |
| 2014/0235976 | A1 | 8/2014 | Bresch et al. |
| 2014/0267718 | A1 | 9/2014 | Govro et al. |
| 2014/0272860 | A1 | 9/2014 | Peterson et al. |
| 2014/0275832 | A1 | 9/2014 | Muehlsteff et al. |
| 2014/0276104 | A1 | 9/2014 | Tao et al. |
| 2014/0330336 | A1 | 11/2014 | Errico et al. |
| 2014/0334697 | A1 | 11/2014 | Kersten et al. |
| 2014/0358017 | A1 | 12/2014 | Op Den Buijs et al. |
| 2014/0378810 | A1 | 12/2014 | Davis et al. |
| 2014/0379369 | A1 | 12/2014 | Kokovidis et al. |
| 2015/0003723 | A1 | 1/2015 | Huang et al. |
| 2015/0068069 | A1 | 3/2015 | Tran et al. |
| 2015/0094597 | A1 * | 4/2015 | Mestha ................ A61B 5/7282 600/407 |
| 2015/0131880 | A1 | 5/2015 | Wang et al. |
| 2015/0157269 | A1 | 6/2015 | Lisogurski et al. |
| 2015/0198707 | A1 | 7/2015 | Al-Alusi |
| 2015/0223731 | A1 | 8/2015 | Sahin |
| 2015/0238150 | A1 | 8/2015 | Subramaniam |
| 2015/0265187 | A1 | 9/2015 | Bernal et al. |
| 2015/0282724 | A1 | 10/2015 | McDuff et al. |
| 2015/0286779 | A1 | 10/2015 | Bala et al. |
| 2015/0301590 | A1 | 10/2015 | Furst et al. |
| 2015/0317814 | A1 | 11/2015 | Johnston et al. |
| 2015/0379370 | A1 | 12/2015 | Clifton et al. |
| 2016/0000335 | A1 | 1/2016 | Khachaturian et al. |
| 2016/0049094 | A1 | 2/2016 | Gupta et al. |
| 2016/0082222 | A1 | 3/2016 | Garcia Molina et al. |
| 2016/0140828 | A1 | 5/2016 | Deforest |
| 2016/0143598 | A1 | 5/2016 | Rusin et al. |
| 2016/0151022 | A1 | 6/2016 | Berlin et al. |
| 2016/0156835 | A1 | 6/2016 | Ogasawara et al. |
| 2016/0174887 | A1 | 6/2016 | Kirenko et al. |
| 2016/0210747 | A1 | 7/2016 | Hay et al. |

(56) References Cited

U.S. PATENT DOCUMENTS

| | | | |
|---|---|---|---|
| 2016/0235344 A1 | 8/2016 | Auerbach | |
| 2016/0310084 A1 | 10/2016 | Banerjee et al. | |
| 2016/0317041 A1 | 11/2016 | Porges et al. | |
| 2016/0345931 A1 | 12/2016 | Xu et al. | |
| 2016/0367186 A1 | 12/2016 | Freeman et al. | |
| 2017/0007342 A1 | 1/2017 | Kasai et al. | |
| 2017/0007795 A1 | 1/2017 | Pedro et al. | |
| 2017/0055877 A1* | 3/2017 | Niemeyer | A61B 5/0077 |
| 2017/0065484 A1 | 3/2017 | Addison et al. | |
| 2017/0071516 A1 | 3/2017 | Bhagat et al. | |
| 2017/0095215 A1 | 4/2017 | Watson et al. | |
| 2017/0095217 A1 | 4/2017 | Hubert et al. | |
| 2017/0119340 A1 | 5/2017 | Nakai et al. | |
| 2017/0147772 A1 | 5/2017 | Meehan et al. | |
| 2017/0164904 A1 | 6/2017 | Kirenko | |
| 2017/0172434 A1 | 6/2017 | Amelard et al. | |
| 2017/0173262 A1 | 6/2017 | Veltz | |
| 2017/0238805 A1 | 8/2017 | Addison et al. | |
| 2017/0238842 A1 | 8/2017 | Jacquel et al. | |
| 2017/0311887 A1 | 11/2017 | Leussler et al. | |
| 2017/0319114 A1 | 11/2017 | Kaestle | |
| 2018/0042486 A1 | 2/2018 | Yoshizawa et al. | |
| 2018/0042500 A1 | 2/2018 | Liao et al. | |
| 2018/0049669 A1 | 2/2018 | Vu et al. | |
| 2018/0053392 A1 | 2/2018 | White et al. | |
| 2018/0104426 A1 | 4/2018 | Oldfield et al. | |
| 2018/0106897 A1 | 4/2018 | Shouldice et al. | |
| 2018/0169361 A1 | 6/2018 | Dennis et al. | |
| 2018/0217660 A1 | 8/2018 | Dayal et al. | |
| 2018/0228381 A1 | 8/2018 | Leboeuf et al. | |
| 2018/0303351 A1 | 10/2018 | Mestha et al. | |
| 2018/0310844 A1 | 11/2018 | Tezuka et al. | |
| 2018/0325420 A1 | 11/2018 | Gigi | |
| 2018/0333050 A1 | 11/2018 | Greiner et al. | |
| 2018/0333102 A1 | 11/2018 | De Haan et al. | |
| 2018/0352150 A1 | 12/2018 | Purwar et al. | |
| 2019/0050985 A1 | 2/2019 | Den Brinker et al. | |
| 2019/0133499 A1 | 5/2019 | Auerbach | |
| 2019/0142274 A1 | 5/2019 | Addison et al. | |
| 2019/0199970 A1 | 6/2019 | Greiner et al. | |
| 2019/0209046 A1* | 7/2019 | Addison | G06T 7/0014 |
| 2019/0209083 A1 | 7/2019 | Wu et al. | |
| 2019/0307365 A1 | 10/2019 | Addison et al. | |
| 2019/0311101 A1 | 10/2019 | Nienhouse | |
| 2019/0343480 A1 | 11/2019 | Shute et al. | |
| 2019/0380599 A1 | 12/2019 | Addison et al. | |
| 2019/0380807 A1 | 12/2019 | Addison et al. | |
| 2020/0046302 A1 | 2/2020 | Jacquel et al. | |
| 2020/0187827 A1 | 6/2020 | Addison et al. | |
| 2020/0202154 A1 | 6/2020 | Wang et al. | |
| 2020/0205734 A1 | 7/2020 | Mulligan et al. | |
| 2020/0237225 A1 | 7/2020 | Addison et al. | |
| 2020/0242790 A1 | 7/2020 | Addison et al. | |
| 2020/0250406 A1 | 8/2020 | Wang et al. | |
| 2020/0253560 A1 | 8/2020 | De Haan | |
| 2020/0279464 A1 | 9/2020 | Llewelyn | |
| 2020/0289024 A1 | 9/2020 | Addison et al. | |
| 2020/0329976 A1 | 10/2020 | Chen et al. | |
| 2020/0409383 A1 | 12/2020 | Maunder | |
| 2021/0068670 A1 | 3/2021 | Redtel | |
| 2021/0142874 A1 | 5/2021 | Llewelyn | |
| 2021/0153746 A1 | 5/2021 | Addison et al. | |
| 2021/0201517 A1 | 7/2021 | Yang et al. | |
| 2021/0233631 A1 | 7/2021 | Llewelyn | |
| 2021/0235992 A1 | 8/2021 | Addison | |
| 2021/0295662 A1 | 9/2021 | Bugbee et al. | |
| 2021/0313075 A1 | 10/2021 | Mc Namara et al. | |
| 2022/0211296 A1 | 7/2022 | Addison et al. | |
| 2023/0122367 A1 | 4/2023 | Tesar | |

FOREIGN PATENT DOCUMENTS

| | | | |
|---|---|---|---|
| CN | 111728602 A | 10/2020 | |
| CN | 112233813 A | 1/2021 | |
| DE | 19741982 A1 | 10/1998 | |
| EP | 2793189 B1 | 11/2016 | |
| EP | 2428162 B1 | 8/2017 | |
| EP | 3207862 A1 | 8/2017 | |
| EP | 3207863 A1 | 8/2017 | |
| EP | 3384827 A1 | 10/2018 | |
| EP | 2772828 B1 | 1/2019 | |
| JP | 2004173010 A | 6/2004 | |
| JP | 2004283373 A | 10/2004 | |
| JP | 3744778 B2 | 12/2005 | |
| JP | 2009544080 A | 12/2009 | |
| JP | 2011130996 A | 7/2011 | |
| KR | 101644843 B1 | 8/2016 | |
| RS | 20120373 A1 | 4/2014 | |
| WO | 2004100067 A2 | 11/2004 | |
| WO | 2005079658 A2 | 9/2005 | |
| WO | 2010034107 A1 | 4/2010 | |
| WO | 2010036653 A1 | 4/2010 | |
| WO | 2015059700 A1 | 4/2015 | |
| WO | 2015078735 A1 | 6/2015 | |
| WO | 2015110859 A1 | 7/2015 | |
| WO | 2016065411 A1 | 5/2016 | |
| WO | 2016178141 A1 | 11/2016 | |
| WO | 2016209491 A1 | 12/2016 | |
| WO | 2017060463 A1 | 4/2017 | |
| WO | 2017089139 A1 | 6/2017 | |
| WO | 2017100188 A2 | 6/2017 | |
| WO | 2017144934 A1 | 8/2017 | |
| WO | 2018042376 A1 | 3/2018 | |
| WO | 2019094893 A1 | 5/2019 | |
| WO | 2019135877 A1 | 7/2019 | |
| WO | 2019240991 A1 | 12/2019 | |
| WO | 2020033613 A1 | 2/2020 | |
| WO | 2021044240 A1 | 3/2021 | |

OTHER PUBLICATIONS

Kwon, Sungjun , et al., "Validation of heart rate extraction using video imaging on a built-in camera system of a smartphone", 34th Annual International Conference of the IEEE EMBS, San Diego, CA, USA, Aug. 28-Sep. 1, 2012, pp. 2174-2177, 4 pages.

Lai, C.J. , et al., "Heated humidified high-flow nasal oxygen prevents intraoperative body temperature decrease in non-intubated thoracoscopy", Journal of Anesthesia, Oct. 15, 2018, 8 pages.

Lawrence, E. , et al., "Data Collection, Correlation and Dissemination of Medical Sensor information in a WSN", IEEE 2009 Fifth International Conference on Networking and Services, 978-0-7695-3586-9/09, Apr. 20, 2009, pp. 402-408, 7 pages.

Li , et al., "A Non-Contact Vision-Based System for Respiratory Rate Estimation", IEEE 978-1-4244-7929-0/14, 2014, pp. 2119-2122, 4 pages.

Liu, H. , et al., "A Novel Method Based on Two Cameras for Accurate Estimation of Arterial Oxygen Saturation", BioMedical Engineering Online, vol. 14, No. 52, 2015, 18 pages.

Liu, Xinyi , et al., "An Image Captioning Method for Infant Sleeping Environment Diagnosis", Springer International Publishing, May 15, 2019, pp. 18-26, 9 pages.

Liu, S. , et al., "In-bed pose estimation: Deep learning with shallow dataset. IEEE journal of translational engineering in health and medicine", IEEE Journal of Translational Engineering in Health and Medicine, No. 7, 2019, pp. 1-12, 12 pages.

Liu, C. , et al., "Motion Magnification", ACM Transactions on Graphics (TOG), vol. 24, No. 3, 2005, pp. 519-526, 8 pages.

Lv , et al., "Class Energy Image Analysis for Video Sensor-Based Gait Recognition: A Review", Sensors, No. 15, 2015, pp. 932-964, 33 pages.

McDuff, Daniel J., et al., "A Survey of Remote Optical Photoplethysmographic Imaging Methods", IEEE 987-1-4244-0270-1/15, 2015, pp. 6398-6404, 7 pages.

Mestha, L.K. , et al., "Towards Continuous Monitoring of Pulse Rate in Neonatal Intensive Care Unit with a Webcam", Proc. of 36th Annual Int. Conf. of the IEEE Engineering in Medicine and Biology Society, Chicago, IL, 2014, pp. 3817-3820, 4 pages.

Mukherjee, S. , et al., "Patient health management system using e-health monitoring architecture", IEEE, International Advance Computing Conference (IACC), 978-1-4799-2572-8/14, Feb. 21, 2014, pp. 400-405, 6 pages.

(56)     References Cited

OTHER PUBLICATIONS

Nguyen , et al., "3D shape, deformation and vibration measurements using infrared Kinect sensors and digital image correlation", Applied Optics, vol. 56, No. 32, Nov. 10, 2017, 8 pages.

Ni , et al., "RGBD-Camera Based Get-Up Event Detection for Hospital Fall Prevention", Acoustics, Speech and Signal Processing (ICASSP) 2012 IEEE International Conf., Mar. 2012, pp. 1405-1408, 6 pages.

Nisar , et al., "Contactless heart rate monitor for multiple persons in a video", IEEE International Conference on Consumer Electronics—Taiwan (ICCE-TW), XP03291229 [Retreived on Jul. 25, 2016], May 27, 2016, 2 pages.

Pereira, C. , et al., "Noncontact Monitoring of Respiratory Rate in Newborn Infants Using Thermal Imaging", IEEE Transactions on Biomedical Engineering, Aug. 23, 2018, 10 pages.

Poh , et al., "Advancements in Noncontact, Multiparameter Physiological Measurements Using a Webcam", IEEE Transactions on Biomedical Engineering, vol. 58, No. 1, Jan. 2011, pp. 7-11, 5 pages.

Poh , et al., "Non-contact, automated cardiac pulse measurements using video imaging and blind source separation", OPT. Express 18, 2010, pp. 10762-10774, 14 pages.

Povsic, Klemen , et al., "Real-Time 3D visualization of the thoracoabdominal surface during breathing with body movement and deformation extraction", Physiological Measurement, vol. 36, No. 7, May 28, 2015, pp. 1497-1516, 22 pages.

Prochazka, et al., "Microsoft Kinect Visual and Depth Sensors for Breathing and Heart Rate Analysis", Senors, vol. 16, No. 7, Jun. 28, 2016, 11 pages.

Rajan, V. , et al., "Clinical Decision Support for Stroke using Multiview Learning based Models for NIHSS Scores", PAKDD 2016 Workshop: Predictive Analytics in Critical Care (PACC), Auckland, New Zealand, 2016, pp. 190-199, 10 pages.

Rajan, V. , et al., "Dependency Clustering of Mixed Data with Gaussian Mixture Copulas", 25th International Joint Conference on Artificial Intelligence IJCAI, New York, USA, 2016, pp. 1967-1973, 7 pages.

Reisner, A. , et al., "Utility of the Photoplethysmogram in Circulatory Monitoring", American Society of Anesthesiologist, May 2008, pp. 950-958, 9 pages.

Reyes, B.A., et al., "Tidal Volume and Instantaneous Respiration Rate Estimation using a Volumetric Surrogate Signal Acquired via a Smartphone Camera", IEEE Journal of Biomedical and Health Informatics, vol. 21(3), Feb. 25, 2016, pp. 764-777, 15 pages.

Rezaei, Mahdi , et al., "DeepSOCIAL: Social Distancing Monitoring and Infection Risk Assessment in COVID-19 Pandemic", Applied Sciences, vol. 10, 7514, Oct. 26, 2020, pp. 1-29, 29 pages.

Rougier, Caroline , et al., "Robust Video Surveillance for Fall Detection Based on Human Shape Deformation", IEEE Transactions on Circuits and Systems for Video Technology, vol. 21, No. 5, May 2011, pp. 611-622, 12 pages.

Rubinstein, M , "Analysis and Visualization of Temporal Variations in Video", Department of Electrical Engineering and Computer Science, Massachusetts Institute of Technology, Feb. 2014, 118 pages.

Sathyamoorthy, Adarsh Jagan, et al., "COVID-Robot: Monitoring Social Distancing Constraints in Crowded Scenarios", Aug. 21, 2020, pp. 1-11, 11 pages.

Scalise, Lorenzo , et al., "Heart rate measurement in neonatal patients using a webcamera", Department of Industrial Engineering and Mathematical Science, Italy, 978-1-4673-0882-3/12, EEE, 2012, 4 pages.

Schaerer, J. , et al., "Multi-dimensional respiratory motion tracking from markerless optical surface imaging based on deformable mesh registration", Physics in Medicine and Biology, vol. 57, No. 2, Dec. 14, 2011, pp. 357-373, 18 pages.

Sengupta, A. , et al., "A Statistical Model for Stroke Outcome Prediction and Treatment Planning", 38th Annual International Conference of the IEE Engineering in Medicine and Biology (Society IEEE EMBC2016), Orlando, USA, 2016, pp. 2516-2519, 4 pages.

Shah, Nitin , et al., "Performance of three new-generation pulse oximeters during motion and low perfusion in volunteers", Journal of Clinical Anesthesia, No. 24, 2012, pp. 385-391, 7 pages.

Shao, Dangdang , et al., "Noncontact Monitoring Breathing Pattern, Exhalation Flow Rate and Pulse Transit Time", EEE Transactions on Biomedical Engineering, vol. 61, No. 11, Nov. 2014, pp. 2760-2767, 8 pages.

Shrivastava, H. , et al., "Classification with Imbalance: A Similarity-based Method for Predicting Respiratory Failure", IEEE International Conference on Bioinformatics and Biomedicine (IEEE BIBM2015), Washington, DC,USA, 2015, pp. 707-714, 8 pages.

Sokooti, Hess , et al., "Hierarchical Prediction of Registration Misalignment Using a Convolutional LSTM: Application to Chest CT Scans", IEEE Access, IEEE, USA, vol. 9, Apr. 20, 2021, 62008-62020, 13 pages.

Srinivas, J. , et al., "A Mutual Authentication Framework for Wireless Medical Sensor Networks", Journal of Medical Systems, 41:80, 2017, pp. 1-19, 19 pages.

Sun, Yu , et al., "Motion-compensated noncontact imaging photoplethysmography to monitor cardiorespiratory status during exercise", Journal of Biomedical Optics, vol. 16, No. 7, Jul. 1, 2011, 10 pages.

Sun, Yu , et al., "Noncontact imaging photoplethysmography to effectively access pulse rate variability", Journal of Biomedical Optics, vol. 18(6), Jun. 2013, 10 pages.

Tamura , et al., "Wearable Photoplethysmographic Sensors-Past & Present", Electronics, vol. 3, 2014, pp. 282-302, 21 pages.

Tarassenko, L. , et al., "Non-contact video-based vital sign monitoring using ambient light and auto-regressive models", Institute of Physics and Engineering in Medicine, vol. 35, 2014, pp. 807-831, 26 pages.

Teichmann, D. , et al., "Non-Contact monitoring techniques-Principles and applications", In Proc. of IEEE International Conference of the Engineering in Medicine and Biology Society (EMBC), San Diego, CA, 2012, pp. 1302-1305, 4 pages.

Transue, S. , et al., "Real-time Tidal vol. Estimation using Isosurface Reconstruction", 2016 IEEE First International Conference on Connected Health: Applications, Systems and Engineering Technologies (CHASE), Jun. 27, 2016, pp. 209-218, 10 pages.

Verkruysee, Wim , et al., "Calibration of Contactless Pulse Oximetry", Anesthesia & Analgesia, vol. 124, No. 1, Jan. 2017, pp. 136-145, 10 pages.

Villarroel, Mauricio , et al., "Continuous non-contact vital sign monitoring in neonatal intensive care unit", Healthcare Technology Letters, vol. 1, Issue 3, 2014, pp. 87-91, 5 pages.

Zhou, J. , et al., "Maximum parsimony analysis of gene copy No. changes in tumor phylogenetics", 15th International Workshop on Algorithms in Bioinformatics WABI 2015, Atlanta, USA, 2015, pp. 108-120, 13 pages.

"European Search Report", European Application No. 17156334.9, Applicant: Covidien LP, Aug. 23, 2017, 10 pages.

"European Search Report", European Patent Application No. 17156337.2, Applicant: Covidien LP, Aug. 23, 2017, 10 pages.

"International Search Report and Written Opinion", International Application No. PCT/US2021/015669, Apr. 12, 2021, 15 pages.

"International Search Report and Written Opinion", International Application No. PCT/US2018/060648, Jan. 28, 2019, 17 pages.

"International Search Report and Written Opinion", International Application No. PCT/US2018/065492, Mar. 8, 2019, 12 pages.

"International Search Report and Written Opinion", International Application No. PCT/US2019/035433, Nov. 11, 2019, 17 pages.

"International Search Report and Written Opinion", International Application No. PCT/US2019/045600, Oct. 23, 2019, 19 pages.

"Invitation to Pay Additional Fees and Partial International Search Report", International Application No. PCT/US2019/035433, Sep. 13, 2019, 16 pages.

"Medical Electrical Equipment, Part 2-61: Particular requirements for basic safety and essential performance of pulse oximeter equipment", BSI Standards Publication, BS EN ISO 80601-2-61, 2011, 98 pages.

(56) References Cited

OTHER PUBLICATIONS

Aarts, Lonneke A.M., et al., "Non-contact heart rate monitoring utilizing camera photoplethysmography in neonatal intensive care unit—A Pilot Study", Early Human Development 89, 2013, pp. 943-948, 6 pages.

Abbas, A.K. , et al., "Neonatal non-contact respiratory monitoring based on real-time infrared thermography", Biomed. Eng. Online, vol. 10, No. 93, 2011, 17 pages.

Addison, Paul S., "A Review of Signal Processing Used in the Implementation of the Pulse Oximetry Photoplethysmographic Fluid Responsiveness Parameter", International Anesthesia Research Society, vol. 119, No. 6, Dec. 2014, pp. 1293-1306, 14 pages.

Addison, Paul S., et al., "Developing an algorithm for pulse oximetry derived respirator rate (RRoxi): a healthy volunteer study", J Clin comput, No. 26, 2012, pp. 45-51, 7 pages.

Addison, Paul S., et al., "Pulse oximetry-derived respiratory rate in general care floor patients", J. Clin Monit Comput, No. 29, 2015, pp. 113-120, 8 pages.

Addison, P.S. , et al., "Video-based Heart Rate Monitoring across a Range of Skin Pigmentations during an Acute Hypoxic Challenge", J Clin Monit Comput, vol. 9, Nov. 9, 2017, 15 pages.

Al-Naji, Ali , et al., "Real Time Apnoea Monitoring of Children Using the Microsoft Kinect Sensor: A Pilot Study", Sensors, 17(286), Feb. 3, 2017, 15 pages.

Amazon , "Dockem Koala Tablet Wall Mount Dock for ipad Air/Mini/Pro, Samsung Galaxy Tab/Note, Nexus 7/10, and More (Black Brackets, Screw-in Version)", https://www.amazon.com/Tablet-Dockem-Samsung-Brackets-Version-dp/B00JV75FC6?th=1, First available Apr. 22, 2014, viewed on Nov. 16, 2021, Apr. 22, 2014, 4 pages.

Amelard , et al., "Non-contact transmittance photoplethysmographic imaging (PPGI) for long-distance cardiovascular monitoring", ResearchGate, XP055542534 [Retrieved online Jan. 15, 2019], Mar. 23, 2015, pp. 1-13, 14 pages.

Armanian, A. M. , "Caffeine administration to prevent apnea in very premature infants", Pediatrics & Neonatology, 57 (5), 2016, pp. 408-412, 5 pages.

Barone, S , et al., "Computer-aided modelling of three-dimensional maxillofacial tissues through multi-modal imaging", Proceedings of the Institution of Mechanical Engineers, Journal of Engineering in Medicine, Part H vol. 227, No. 2, Feb. 1, 2013, 1 page.

Barone, S , et al., "Creation of 3D Multi-body Orthodontic Models by Using Independent Imaging Sensors", Senros MDPI AG Switzerland, vol. 13, No. 2, Jan. 1, 2013, pp. 2033-2050, 18 pages.

Bartula, M. , et al., "Camera-based System for Sontactless Monitoring of Respiration", 2013 35th Annual International Conference of the IEEE Engineering in Medicine and Biology Society (EMBC), Jul. 3, 2013, pp. 2672-2675, 4 pages.

Bhattacharya, S. , et al., "A Novel Classification Method for Predicting Acute Hypotensive Episodes in Critical Care", 5th ACM Conference on Bioinformatics, Computational Bilogy and Health Informatics (ACM-BCB 2014), Newport Beach, USA, 2014, 10 pages.

Bhattacharya, S. , et al., "Unsupervised learning using Gaussian Mixture Copula models", 21st International Conference on Computational Statistics (COMPSTAT 2014), Geneva, Switzerland, 2014, pp. 523-530, 8 pages.

Bickler, Philip E., et al., "Factors Affecting the Performance of 5 Cerebral Oximeters During Hypoxia in Healthy Volunteers", Society for Technology in Anesthesia, vol. 117, No. 4, Oct. 2013, pp. 813-823, 11 pages.

Bousefsaf, Frederic , et al., "Continuous wavelet filtering on webcam photoplethysmographic signals to remotely assess the instantaneous heart rate", Biomedical Signal Processing and Control 8, 2013, pp. 568-574, 7 pages.

Bruser, C. , et al., "Adaptive Beat-to-Beat Heart Rate Estimation in Ballistocardiograms", IEEE Transactions Information Technology in Biomedicine, vol. 15, No. 5, Sep. 2011, pp. 778-786, 9 pages.

Cennini, Giovanni , et al., "Heart rate monitoring via remote photoplethysmography with motion artifacts reduction", Optics Express, vol. 18, No. 5, Mar. 1, 2010, pp. 4867-4875, 9 pages.

Colantonio, S. , et al., "A smart mirror to promote a healthy lifestyle", Biosystems Engineering. vol. 138, Innovations in Medicine and Healthcare, Oct. 2015, pp. 33-43, 11 pages.

Cooley , et al., "An Alorithm for the Machine Calculation of Complex Fourier Series", Aug. 17, 1964, pp. 297-301, 5 pages.

Di Fiore, J.M. , et al., "Intermittent hypoxemia and oxidative stress in preterm infants", Respiratory Physiology & Neurobiology, No. 266, 2019, pp. 121-129, 25 pages.

Fei, J. , et al., "Thermistor at a distance: unobtrusive measurement of breathing", IEEE Transactions on Biomedical Engineering, vol. 57, No. 4, 2010, pp. 968-998, 11 pages.

Feng, Litong , et al., "Dynamic ROI based on K-means for remote photoplethysmography", IEE International Conference on Accoustics, Speech and Signal Processing (ICASSP), Apr. 2015, pp. 1310-1314, 5 pages.

Fischer , et al., "ReMoteCare: Health Monitoring with Streaming Video", OCMB '08, 7th International Conference on Mobile Business, IEEE, Piscataway, NJ,, Jul. 7, 2008, pp. 280-286.

George , et al., "Respiratory Rate Measurement From PPG Signal Using Smart Fusion Technique", International Conference on Engineering Trends and Science & Humanities (ICETSH-2015), 2015, 5 pages.

Goldman, L.J. , "Nasal airflow and thoracoabdominal motion in children using infrared thermographic video processing", Pediatric Pulmonology, vol. 47, No. 5, 2012, pp. 476-486, 11 pages.

Grimm, T. , et al., "Sleep position classification from a depth camera using bed aligned maps", 23rd International Conference on Pattern Recognition (ICPR), Dec. 2016, pp. 319-324, 6 pages.

GSMARENA , "Apple iPad Pro 11 (2018)", https://www.gsmarena.com/apple_ipad_pro_11_(2018)-9386.pjp, viewed on Nov. 16, 2021, 1 page.

Guazzi, Alessandro R., et al., "Non-contact measurement of oxygen saturation with an RGB camera", Biomedical Optics Express, vol. 6, No. 9, Sep. 1, 2015, pp. 3320-3338, 19 pages.

Han, J. , et al., "Visible and infrared image registration in man-made environments employing hybrid visuals features", Pattern Recognition Letters, vol. 34, No. 1, 2013, pp. 42-51, 10 pages.

Harte, James M., et al., "Chest wall motion analysis in healthy volunteers and adults with cystic fibrosis using a novel Kinect-based motion tracking system", Medical & Biological Engineering & Computing, 54(11), Feb. 13, 2016, pp. 1631-1640, 11 pages.

Huddar, V. , et al., "Predicting Postoperative Acute Respiratory Failure in Critical Care using Nursing Notes and Physiological Signals", 36th Annual International Conference of IEEE Engineering in Medicine and Biology Society (IEEE EMBC 2014), Chicago, USA, 2014, pp. 2702-2705, 4 pages.

Hyvarinen, A. , et al., "Independent Component Analysis: Algorithms and Applications", Neural Networks, vol. 13, No. 4, 2000, pp. 411-430, 31 pages.

Zaunseder , et al., "Spatio-temporal analysis of blood perfusion by imaging photoplethysmography", Progress in Biomedical Optics and Imaging, SPIE—International Society for Optical Engineering, vol. 10501, Feb. 20, 2018, 15 pages.

Zhou, J. , et al., "Maximum parsimony analysis of gene copy number changes in tumor phylogenetics", 15th International Workshop on Algorithms in Bioinformatics WABI 2015, Atlanta, USA, 2015, pp. 108-120, 13 pages.

Javadi, M. , et al., "Diagnosing Pneumonia in Rural Thailand: Digital Cameras versus Film Digitizers for Chest Radiograph Teleradiology", International Journal of Infectious Disease, 10(2), Mar. 2006, pp. 129-135, 7 pages.

Jopling, M. W., et al., "Issues in the Laboratory Evaluation of Pulse Oximeter Performance", Anesth. Analg., No. 94, 2002, pp. S62-S68, 7 pages.

Kastle, Siegfried W., et al., "Determining the Artifact Sensitivity of Recent Pulse Oximeters During Laboratory Benchmarking", Journal of Clinical Monitoring and Computing, vol. 16, No. 7, 2000, pp. 509-552, 14 pages.

Klaessens, J.H.G.M. , et al., "Non-invasive skin oxygenation imaging using a multi-spectral camera system: Effectiveness of various

(56) References Cited

OTHER PUBLICATIONS concentration algorithms applied on human skin", Proc. of SPIE, vol. 7174 717408-1, 2009, 14 pages.

Kong, Lingqin , et al., "Non-contact detection of oxygen saturation based on visible light imaging device using ambient light", Optics Express, vol. 21, No. 15, Jul. 29, 2013, pp. 17646-17471, 8 pages.

Kortelainen, J.M. , et al., "Sleep staging based on signals acquired through bed sensor", IEEE Transactions on Informational Technology in Biomedicine, vol. 14, No. 3, May 2010, pp. 776-785, 10 pages.

Kumar, M. , et al., "Distance PPG: Robust non-contact vital signs monitoring using a camera", Biomedical Optics Express, vol. 6, No. 5, May 1, 2015, 24 pages.

Japanese Invitation to Correct Deficiencies, 19 758 562.3-1113, Sep. 16, 2024, 11 pgs.

Wadhwa, N. , et al., "Phase-Based Video Motion Processing", MIT Computer Science and Artificial Intelligence Lab, Jul. 2013, 9 pages.

Wadhwa, N. , et al., "Riesz pyramids for fast phase-based video magnification", In Proc. of IEEE International Conference on Computational Photography (ICCP), Santa Clara, CA, 2014, 10 pages.

Wang, W. , et al., "Exploiting spatial redundancy of image sensor for motion robust rPPG", IEEE Transactions on Biomedical Engineering, vol. 62, No. 2, 2015, pp. 415-425, 11 pages.

Wu, H.Y. , et al., "Eulerian video magnifcation for revealing subtle changes in the world", ACM Transactions on Graphics (TOG), vol. 31, No. 4, 2012, pp. 651-658, 8 pages.

Wulbrand, H. , et al., "Submental and diaphragmatic muscle activity during and at resolution of mixed and obstructive apneas and cardiorespiratory arousal in preterm infants", Pediatric Research, No. 38(3), 1995, pp. 298-305, 9 pages.

Yu, M.C. , et al., "Noncontact Respiratory Measurement of Volume Change Using Depth Camera", 2012 Annual International Conference of the IEEE Engeineering in Medicine and Biology Society, Aug. 28, 2012, pp. 2371-2374, 4 pages.

* cited by examiner

VIDEO-BASED PATIENT MONITORING SYSTEMS AND ASSOCIATED METHODS FOR DETECTING AND MONITORING BREATHING

CROSS-REFERENCE TO RELATED APPLICATIONS

This application is a continuation application of U.S. application Ser. No. 17/656,597 filed Mar. 25, 2022, now U.S. Pat. No. 12,016,655, which is a continuation application of U.S. application Ser. No. 16/535,228, filed Aug. 8, 2019, now U.S. Pat. No. 11,311,252, which claims the benefit of U.S. Provisional Application No. 62/716,724, filed Aug. 9, 2018, which is specifically incorporated by reference herein for all that it discloses or teaches.

FIELD

The present technology is generally related to video-based patient monitoring and to detection and monitoring of breathing of patients.

BACKGROUND

Many conventional medical monitors require attachment of a sensor to a patient in order to detect physiologic signals from the patient and to transmit detected signals through a cable to the monitor. These monitors process the received signals and determine vital signs such as the patient's pulse rate, respiration rate, and arterial oxygen saturation. For example, a pulse oximeter is a finger sensor that can include two light emitters and a photodetector. The sensor emits light into the patient's finger and transmits the detected light signal to a monitor. The monitor includes a processor that processes the signal, determines vital signs (e.g., pulse rate, respiration rate, arterial oxygen saturation), and displays the vital signs on a display.

Other monitoring systems include other types of monitors and sensors, such as electroencephalogram (EEG) sensors, blood pressure cuffs, temperature probes, air flow measurement devices (e.g., spirometer), and others. Some wireless, wearable sensors have been developed, such as wireless EEG patches and wireless pulse oximetry sensors.

Video-based monitoring is a field of patient monitoring that uses one or more remote video cameras to detect physical attributes of the patient. This type of monitoring can also be called "non-contact" monitoring in reference to the remote video sensor(s), which does/do not contact the patient. The remainder of this disclosure offers solutions and improvements in this field.

SUMMARY

The techniques of this disclosure generally relate to the field of medical monitoring, and, in particular, to non-contact detecting and monitoring of patient breathing.

In one aspect, the present disclosure provides systems, methods, and computer readable media for calculating a change in depth of regions in one or more regions of interest (ROI's) on a patient and assigning one or more visual indicators to the regions based on the calculated changes in depth of the regions over time.

In one aspect, a video-based patient monitoring system includes at least one processor configured to define one or more regions of interest (ROI's) on a patient and a non-contact detector having at least one image capture device.

The at least one image capture device is configured to capture two or more images of the one or more ROI's. The at least one processor is further configured to: calculate a change in depth of a region of at least one of the one or more ROI's within the two or more images and assign one or more visual indicators from a predetermined visual scheme to the region of the at least one ROI based at least in part on the calculated change in depth of the region within the two or more images.

In one aspect, a method includes capturing two or more images of a patient, calculating a change in depth of regions on the patient within the two or more images; and assigning one or more visual indicators from a predetermined visual scheme to the regions based at least in part on the calculated changes in depth of the regions.

In another aspect, the disclosure provides one or more breathing parameter signals corresponding to the regions of interest that can be generated and/or analyzed. In further aspects, the one or more visual indicators can be displayed overlaid onto the regions in real-time. In additional aspects, the systems, methods, and/or computer readable media (i) can display one or more generated breathing parameter signals in real-time and/or (ii) can trigger an alert and/or an alarm when a breathing abnormality is detected.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure. The drawings should not be taken to limit the disclosure to the specific embodiments depicted, but are for explanation and understanding only.

DETAILED DESCRIPTION

Figure 1:
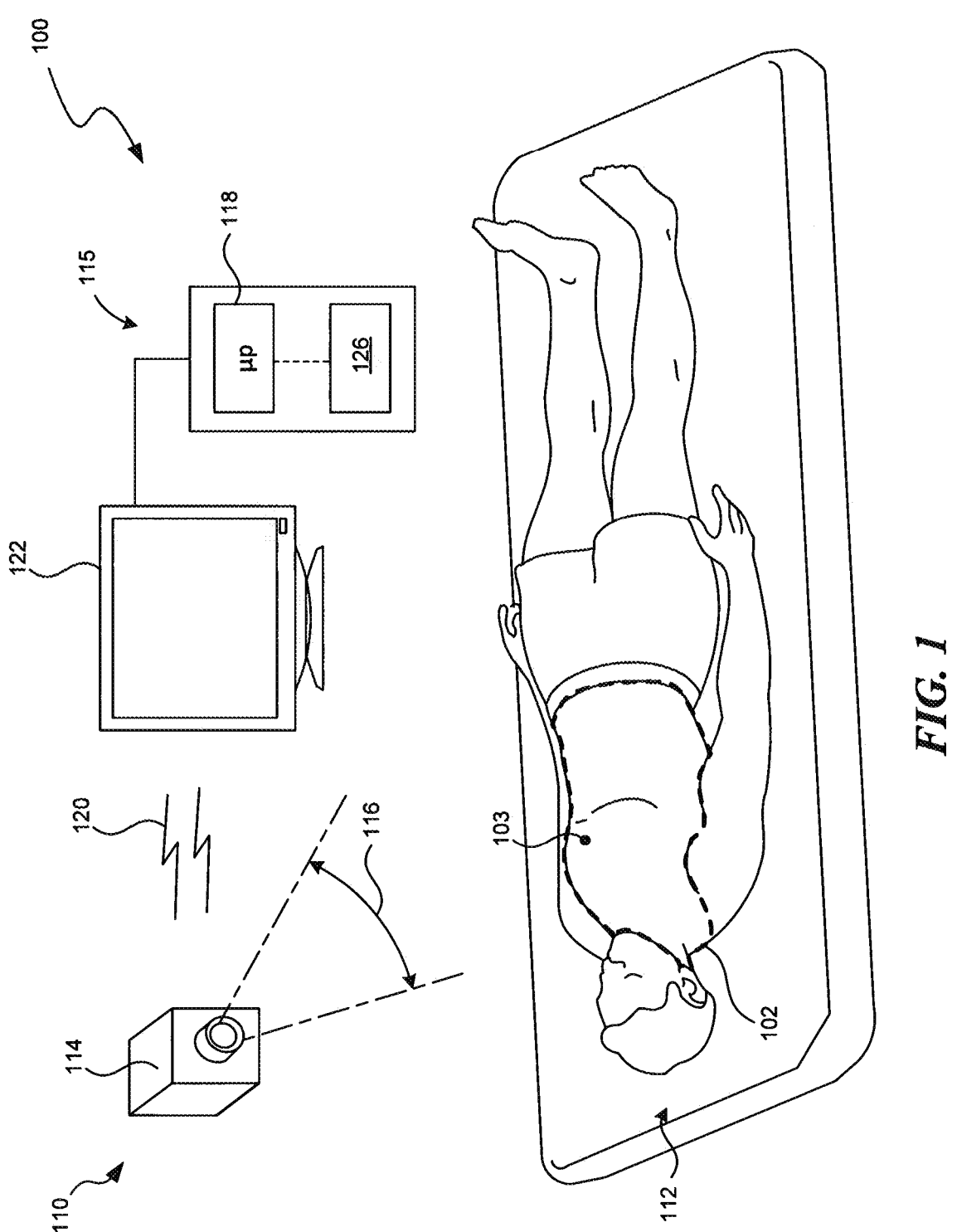
FIG. 1 is a schematic view that illustrates a video-based patient monitoring system configured in accordance with various embodiments of the present technology.

The following disclosure describes video-based patient monitoring systems and associated methods for detecting and/or monitoring patient breathing. As described in greater detail below, systems and/or methods configured in accordance with embodiments of the present technology are configured to recognize and/or identify a patient and to define one or more regions of interest (ROI's) on the patient. Additionally or alternatively, the system and/or methods are configured to capture one or more images (e.g., a video sequence) of the ROI's and/or to measure changes in depth of regions (e.g., one or more pixels or groups of pixels) in the ROI's over time. Based, at least in part, on these measurements, the systems and/or methods can assign one or more visual indicators to regions of one or more of the ROI's. In these and other embodiments, the systems and/or methods generate various breathing parameter signals of all or a subset of the ROI's. The breathing parameter signals can include tidal volume, minute volume, and/or respiratory rate, among others. In these and other embodiments, the systems and/or methods can analyze the generated signals and can trigger alerts and/or alarms when the systems and/or methods detect one or more breathing abnormalities. In these and still other embodiments, the systems and/or methods can display (e.g., in real-time) all or a subset of the assigned visual indicator(s) and/or of the generated signals on a display, e.g., to provide a user (e.g., a caregiver, a clinician, a patient, etc.) a visual indication of the patient's breathing. For example, the systems and/or methods can overlay the assigned visual indicator(s) onto the captured images of the patient to indicate (i) whether the patient is breathing and/or, (ii) whether a patient's breathing is abnormal.

Specific details of several embodiments of the present technology are described herein with reference to FIGS. 1-11. Although many of the embodiments are described with respect to devices, systems, and methods for video-based detection and/or monitoring of breathing in a human patient, other applications and other embodiments in addition to those described herein are within the scope of the present technology. For example, at least some embodiments of the present technology can be useful for video-based detection and/or monitoring of breathing in other animals and/or in non-patients (e.g., elderly or neonatal individuals within their homes). It should be noted that other embodiments in addition to those disclosed herein are within the scope of the present technology. Further, embodiments of the present technology can have different configurations, components, and/or procedures than those shown or described herein. Moreover, a person of ordinary skill in the art will understand that embodiments of the present technology can have configurations, components, and/or procedures in addition to those shown or described herein and that these and other embodiments can be without several of the configurations, components, and/or procedures shown or described herein without deviating from the present technology.

FIG. 1 is a schematic view of a patient 112 and a video-based patient monitoring system 100 configured in accordance with various embodiments of the present technology. The system 100 includes a non-contact detector 110 and a computing device 115. In some embodiments, the detector 110 can include one or more image capture devices, such as one or more video cameras. In the illustrated embodiment, the non-contact detector 110 includes a video camera 114. The non-contact detector 110 of the system 100 is placed remote from the patient 112. More specifically, the video camera 114 of the non-contact detector 110 is positioned remote from the patient 112 in that it is spaced apart from and does not contact the patient 112. The camera 114 includes a detector exposed to a field of view (FOV) 116 that encompasses at least a portion of the patient 112.

The camera 114 can capture a sequence of images over time. The camera 114 can be a depth sensing camera, such as a Kinect camera from Microsoft Corp. (Redmond, Washington). A depth sensing camera can detect a distance between the camera and objects within its field of view. Such information can be used, as disclosed herein, to determine that a patient 112 is within the FOV 116 of the camera 114 and/or to determine one or more regions of interest (ROI's) to monitor on the patient 112. Once a ROI is identified, the ROI can be monitored over time, and the changes in depth of regions (e.g., pixels) within the ROI 102 can represent movements of the patient 112 associated with breathing. As described in greater detail in U.S. Provisional Patent Application Ser. No. 62/614,763, those movements, or changes of regions within the ROI 102, can be used to determine various breathing parameters, such as tidal volume, minute volume, respiratory rate, etc. U.S. Provisional Patent Application Ser. No. 62/614,763 is incorporated herein by reference in its entirety.

In some embodiments, the system 100 determines a skeleton outline of the patient 112 to identify a point or points from which to extrapolate a ROI. For example, a skeleton can be used to find a center point of a chest, shoulder points, waist points, and/or any other points on a body of the patient 112. These points can be used to determine one or more ROI's. For example, a ROI 102 can be defined by filling in area around a center point 103 of the chest, as shown in FIG. 1. Certain determined points can define an outer edge of the ROI 102, such as shoulder points. In other embodiments, instead of using a skeleton, other points are used to establish a ROI. For example, a face can be recognized, and a chest area inferred in proportion and spatial relation to the face. In other embodiments, the system 100 can define a ROI around a point using parts of the patient 112 that are within a range of depths from the camera 114. In other words, once the system 100 determines a point from which to extrapolate a ROI, the system 100 can utilize depth information from the depth sensing camera 114 to fill out the ROI. For example, if the point 103 on the chest is selected, parts of the patient 112 around the point 103 that are a similar depth from the camera 114 as the point 103 are used to determine the ROI 102.

In another example, the patient 112 can wear specially configured clothing (not shown) that includes one or more features to indicate points on the body of the patient 112, such as the patient's shoulders and/or the center of the patient's chest. The one or more features can include visually encoded message (e.g., bar code, QR code, etc.), and/or brightly colored shapes that contrast with the rest of the patient's clothing. In these and other embodiments, the one or more features can include one or more sensors that are configured to indicate their positions by transmitting light or other information to the camera 114. In these and still other embodiments, the one or more features can include a grid or another identifiable pattern to aid the system 100 in recognizing the patient 112 and/or the patient's movement. In some embodiments, the one or more features can be stuck on the clothing using a fastening mechanism such as adhesive, a pin, etc. For example, a small sticker can be placed on a patient's shoulders and/or on the center of the patient's chest that can be easily identified within an image captured by the camera 114. The system 100 can recognize the one or more features on the patient's clothing to identify specific points on the body of the patient 112. In turn, the system 100 can use these points to recognize the patient 112 and/or to define a ROI.

In some embodiments, the system 100 can receive user input to identify a starting point for defining a ROI. For example, an image can be reproduced on a display 122 of the system 100, allowing a user of the system 100 to select a patient 112 for monitoring (which can be helpful where multiple objects are within the FOV 116 of the camera 114) and/or allowing the user to select a point on the patient 112 from which a ROI can be determined (such as the point 103 on the chest of the patient 112). In other embodiments, other methods for identifying a patient 112, identifying points on the patient 112, and/or defining one or more ROI's can be used.

Figure 2:
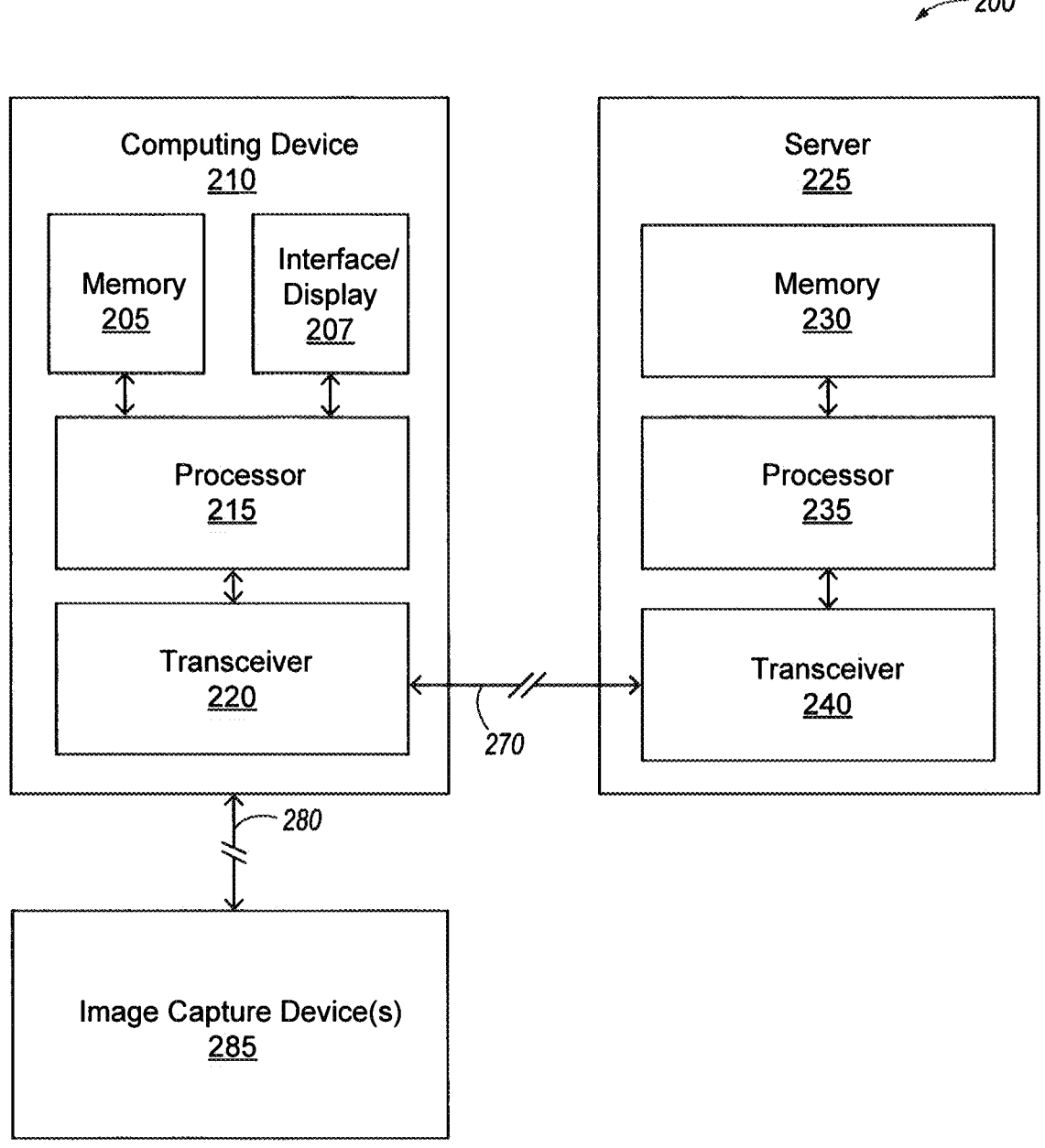
FIG. 2 is a block diagram that illustrates a video-based patient monitoring system having a computing device, a server, and one or more image capture devices, and configured in accordance with various embodiments of the present technology.

The images detected by the camera 114 can be sent to the computing device 115 through a wired or wireless connection 120. The computing device 115 can include a processor 118 (e.g., a microprocessor), the display 122, and/or hardware memory 126 for storing software and computer instructions. Sequential image frames of the patient 112 are recorded by the video camera 114 and sent to the processor 118 for analysis. The display 122 can be remote from the camera 114, such as a video screen positioned separately from the processor 118 and the memory 126. Other embodiments of the computing device 115 can have different, fewer, or additional components than shown in FIG. 1. In some embodiments, the computing device 115 can be a server. In other embodiments, the computing device 115 of FIG. 1 can be additionally connected to a server (e.g., as shown in FIG. 2 and discussed in greater detail below). The captured images/video can be processed or analyzed at the computing device 115 and/or a server to determine a variety of parameters (e.g., tidal volume, minute volume, respiratory rate, etc.) of a patient's breathing.

FIG. 2 is a block diagram illustrating a video-based patient monitoring system 200 (e.g., the video-based patient monitoring system 100 shown in FIG. 1) having a computing device 210, a server 225, and one or more image capture devices 285, and configured in accordance with various embodiments of the present technology. In various embodiments, fewer, additional, and/or different components can be used in the system 200. The computing device 210 includes a processor 215 that is coupled to a memory 205. The processor 215 can store and recall data and applications in the memory 205, including applications that process information and send commands/signals according to any of the methods disclosed herein. The processor 215 can also (i) display objects, applications, data, etc. on an interface/display 207 and/or (ii) receive inputs through the interface/display 207. As shown, the processor 215 is also coupled to a transceiver 220.

The computing device 210 can communicate with other devices, such as the server 225 and/or the image capture device(s) 285 via (e.g., wired or wireless) connections 270 and/or 280, respectively. For example, the computing device 210 can send to the server 225 information determined about a patient from images captured by the image capture device(s) 285. The computing device 210 can be the computing device 115 of FIG. 1. Accordingly, the computing device 210 can be located remotely from the image capture device(s) 285, or it can be local and close to the image capture device(s) 285 (e.g., in the same room). In various embodiments disclosed herein, the processor 215 of the computing device 210 can perform the steps disclosed herein. In other embodiments, the steps can be performed on a processor 235 of the server 225. In some embodiments, the various steps and methods disclosed herein can be performed by both of the processors 215 and 235. In some embodiments, certain steps can be performed by the processor 215 while others are performed by the processor 235. In some embodiments, information determined by the processor 215 can be sent to the server 225 for storage and/or further processing.

In some embodiments, the image capture device(s) 285 are remote sensing device(s), such as depth sensing video camera(s), as described above with respect to FIG. 1. In some embodiments, the image capture device(s) 285 can be or include some other type(s) of device(s), such as proximity sensors or proximity sensor arrays, heat or infrared sensors/cameras, sound/acoustic or radiowave emitters/detectors, or other devices that include a field of view and can be used to monitor the location and/or characteristics of a patient or a region of interest (ROI) on the patient. Body imaging technology can also be utilized according to the methods disclosed herein. For example, backscatter x-ray or millimeter wave scanning technology can be utilized to scan a patient, which can be used to define and/or monitor a ROI. Advantageously, such technologies can be able to "see" through clothing, bedding, or other materials while giving an accurate representation of the patient's skin. This can allow for more accurate measurements, particularly if the patient is wearing baggy clothing or is under bedding. The image capture device(s) 285 can be described as local because they are relatively close in proximity to a patient such that at least a part of a patient is within the field of view of the image capture device(s) 285. In some embodiments, the image capture device(s) 285 can be adjustable to ensure that the patient is captured in the field of view. For example, the image capture device(s) 285 can be physically movable, can have a changeable orientation (such as by rotating or panning), and/or can be capable of changing a focus, zoom, or other characteristic to allow the image capture device(s) 285 to adequately capture images of a patient and/or a ROI of the patient. In various embodiments, for example, the image capture device(s) 285 can focus on a ROI, zoom in on the ROI, center the ROI within a field of view by moving the image capture device(s) 285, or otherwise adjust the field of view to allow for better and/or more accurate tracking/measurement of the ROI.

The server 225 includes a processor 235 that is coupled to a memory 230. The processor 235 can store and recall data and applications in the memory 230. The processor 235 is also coupled to a transceiver 240. In some embodiments, the processor 235, and subsequently the server 225, can communicate with other devices, such as the computing device 210 through the connection 270.

The devices shown in the illustrative embodiment can be utilized in various ways. For example, either the connections 270 and 280 can be varied. Either of the connections 270 and 280 can be a hard-wired connection. A hard-wired connection can involve connecting the devices through a USB (universal serial bus) port, serial port, parallel port, or other type of wired connection that can facilitate the transfer of data and information between a processor of a device and a second processor of a second device. In another embodiment, either of the connections 270 and 280 can be a dock where one device can plug into another device. In other embodiments, either of the connections 270 and 280 can be a wireless connection. These connections can take the form of any sort of wireless connection, including, but not limited to, Bluetooth connectivity, Wi-Fi connectivity, infrared, visible light, radio frequency (RF) signals, or other wireless protocols/methods. For example, other possible modes of wireless communication can include near-field communications, such as passive radio-frequency identification (RFID) and active RFID technologies. RFID and similar near-field communications can allow the various devices to communicate in short range when they are placed proximate to one another. In yet another embodiment, the various devices can connect through an internet (or other network) connection. That is, either of the connections 270 and 280 can represent several different computing devices and network components that allow the various devices to communicate through the internet, either through a hard-wired or wireless connection. Either of the connections 270 and 280 can also be a combination of several modes of connection.

The configuration of the devices in FIG. 2 is merely one physical system 200 on which the disclosed embodiments can be executed. Other configurations of the devices shown can exist to practice the disclosed embodiments. Further, configurations of additional or fewer devices than the devices shown in FIG. 2 can exist to practice the disclosed embodiments. Additionally, the devices shown in FIG. 2 can be combined to allow for fewer devices than shown or can be separated such that more than the three devices exist in a system. It will be appreciated that many various combinations of computing devices can execute the methods and systems disclosed herein. Examples of such computing devices can include other types of medical devices and sensors, infrared cameras/detectors, night vision cameras/detectors, other types of cameras, augmented reality goggles, virtual reality goggles, mixed reality goggle, radio frequency transmitters/receivers, smart phones, personal computers, servers, laptop computers, tablets, blackberries, RFID enabled devices, smart watch or wearables, or any combinations of such devices.

Figure 3:
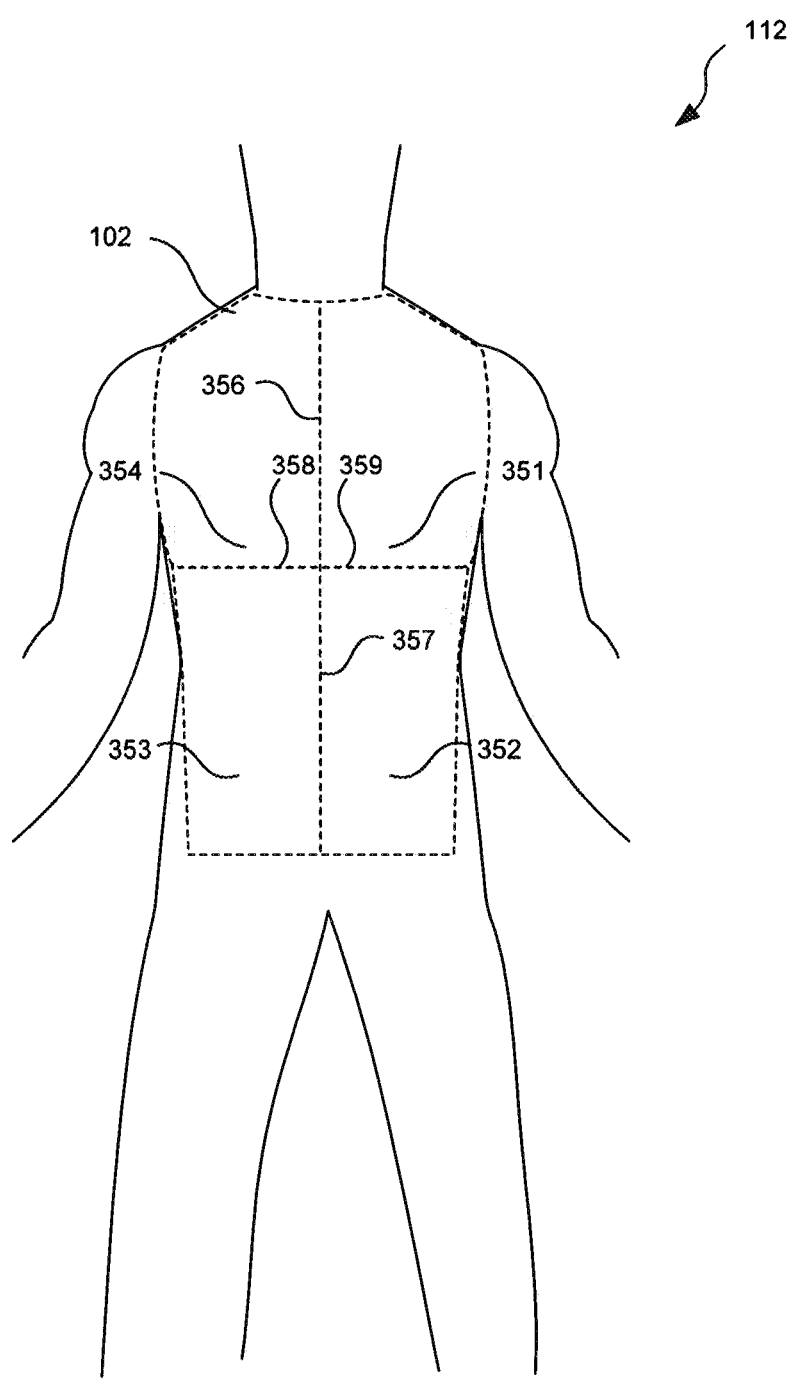
FIG. 3 is a schematic view of a patient that illustrates various regions of interest that can be defined by video-based patient monitoring systems configured in accordance with various embodiments of the present technology.

FIG. 3 is a schematic view of a patient 112 showing various regions of interest (ROI's) that can be defined by video-based patient monitoring systems configured in accordance with various embodiments of the present technology. As discussed above, a video-based patient monitoring system can define a ROI using a variety of methods (e.g., using extrapolation from a point on the patient 112, using inferred positioning from proportional and/or spatial relationships with the patient's face, using parts of the patient 112 having similar depths from the camera 114 as a point, using one or more features on the patient's clothing, using user input, etc.). In some embodiments, the video-based patient monitoring system can define an aggregate ROI 102 that includes both sides of the patient's chest as well as both side of the patient's abdomen. As discussed in greater detail below, the aggregate ROI 102 can be useful in determining a patient's aggregate tidal volume, minute volume, and/or respiratory rate, among other aggregate breathing parameters. In these and other embodiments, the system 100 can define one or more smaller regions of interest within the patient's torso. For example, the system 100 can define ROI's 351-354. As shown, ROI 351 corresponds to the left half of the patient's chest, ROI 352 corresponds to the left half of the patient's abdomen, ROI 353 corresponds to the right half of the patient's abdomen, and ROI 354 corresponds to the right half of the patient's chest.

In these and other embodiments, the system 100 can define other regions of interest in addition to or in lieu of the ROI's 102, 351, 352, 353, and/or 354. For example, the system 100 can define a ROI 356 corresponding to the patient's chest (e.g., the ROI 351 plus the ROI 354) and/or a ROI 357 corresponding to the patient's abdomen (e.g., the ROI 352 plus the ROI 353). As discussed in greater detail below, the system 100 can use ROI's 351, 352, 353, 354, 356 and/or 357 to detect paradoxical breathing of the patient 112. In these and other embodiments, the system 100 can define a ROI 358 corresponding to the right side of the patient's chest or torso (e.g., the ROI 353 and/or the ROI 354) and/or a ROI 359 corresponding to the left side of the patient's chest or torso (e.g., the ROI 351 and/or the ROI 352). As described in greater detail below, the system 100 can use the ROI's 351, 352, 353, 354, 358, and/or 359 to detect asymmetric breathing across the patient's chest (e.g., due to a collapsed lung). In these and still other embodiments, the system 100 can define one or more other regions of interest than shown in FIG. 3. For example, the system 100 can define a region of interest that includes other parts of the patient's body, such as at least a portion of the patient's neck (e.g., to detect when the patient 112 is straining to breathe).

Figure 4B:
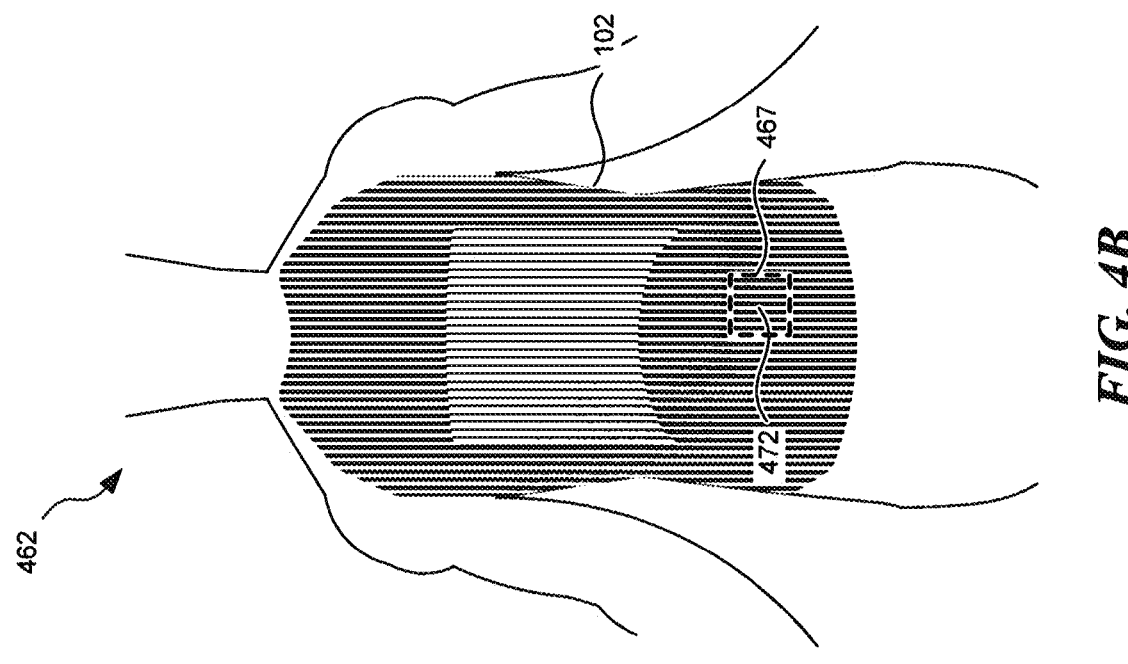
FIGS. 4A and 4B are schematic views that illustrate images of regions of interest generated from images captured using an image capture device of a video-based patient monitoring system configured in accordance with various embodiments of the present technology.
Figure 4A:
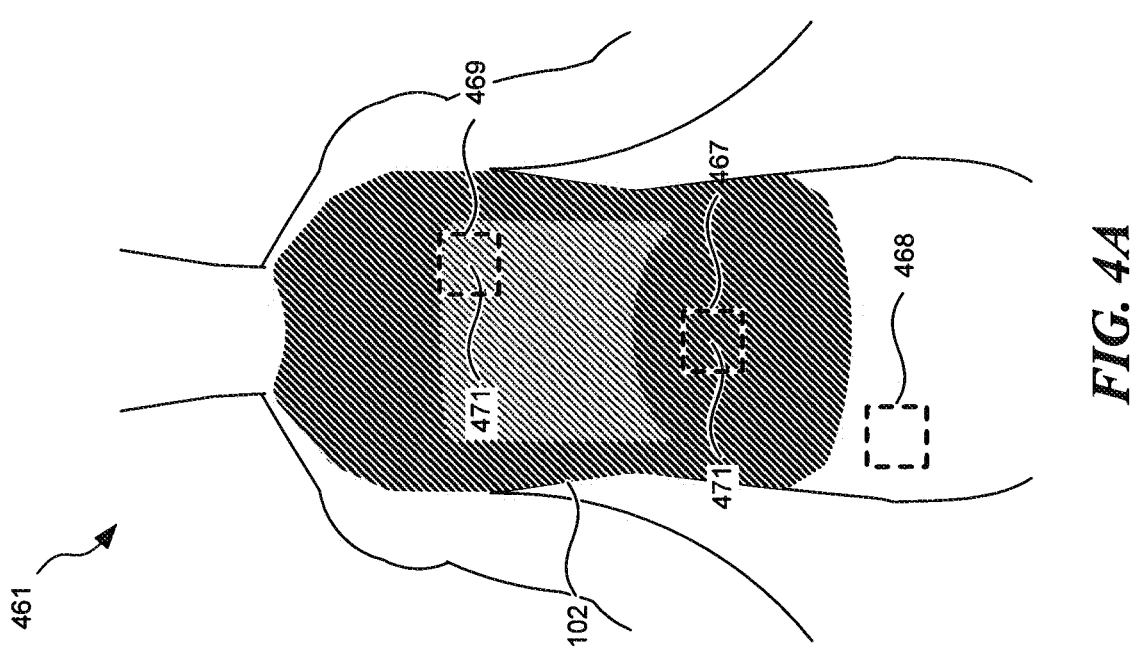

FIGS. 4A and 4B are schematic views of images 461 and 462, respectively, of an aggregate ROI 102. The images 461 and 462 can be generated from images of the ROI 102 captured using an image capture device of a video-based patient monitoring system configured in accordance with various embodiments of the present technology. In some embodiments, the video-based patient monitoring system can capture images of the ROI 102 by directing the image capture device toward the ROI 102 and capturing a sequence of two or more images (e.g., a video sequence) of the ROI 102. As described in greater detail below, the generated image 461 illustrates outward movement (e.g., in real-time) of a patient's torso within the ROI 102, whereas the generated image 462 illustrates inward movement (e.g., in real-time) of the patient's torso within the ROI 102.

Using two images of the two or more captured images, the system can calculate change(s) in depth over time between the image capture device and one or more regions (e.g., one or more pixels or groups of pixels) within a ROI. For example, the system can compute a difference between a first depth of a first region 467 in the ROI 102 in a first image of the two or more captured images and a second depth of the first region 467 in the ROI 102 in a second image of the two or more captured images. In some embodiments, the system can assign visual indicators (e.g., colors, patterns, shades, concentrations, intensities, etc.) from a predetermined visual scheme to regions in an ROI. The visual indicators can correspond to changes in depth of computed by the system (e.g., to the signs and/or magnitudes of computed changes in depth). As shown in FIGS. 4A and 4B, for example, the system can assign (i) a first pattern 471 to regions (e.g., to regions 467 and 469 in the image 461) in the ROI 102 that the system determines have moved toward the image capture device over time (e.g., that have exhibited negative changes in depth across two captured images), (ii) a second pattern 472 to regions (e.g., to region 467 in the image 462) in the ROI 102 that the system determines have moved away from the image capture device over time (e.g., that have exhibited positive changes in depth across two captured images), and/or (iii) no pattern to regions (e.g., to region 468 in the image 461) in the ROI 102 that the system determines have not moved toward or away from the image capture device over time (e.g., that have exhibited negligible changes in depth and/or changes in depth equivalent to zero across two images). In these and other embodiments, the system can assign a new pattern or no pattern to regions that exhibit changes in depth that the system determines are not physiological and/or are not related to respiratory motion (e.g., changes in depth that are too quick, changes in depth indicative of gross body movement, etc.).

In these and other embodiments, the concentration (e.g., the density) of the assigned patterns can be positively correlated with the magnitude of a computed change in depth. As shown in FIG. 4A, for example, the concentration of the first pattern 471 assigned to the region 467 in the image 461 is much greater than the concentration of the first pattern 471 assigned to the region 469. In other words, the portion of the patient's body that corresponds to the region 467 in the image 461 exhibited a greater change in depth toward the image capture device of the system over time than the portion of the patient's body that corresponds to the region 469 in the image 461.

Although the visual indicators displayed in the images 461 and 462 illustrated in FIGS. 4A and 4B, respectively, are patterns with varying concentrations, video-based patient monitoring systems configured in accordance with other embodiments of the present technology can use other visual indicators, such as colors, shades, and/or varying degrees of intensity, to visually depict changes in depth over time. For example, a video-based patient monitoring system can assign (i) a first color (e.g., green) to regions in the ROI that the system determines have moved toward the image capture device over time (e.g., that have exhibited negative changes in depth across two captured images) and (ii) a second color (e.g., red) to regions in the ROI that the system determines have moved away from the image capture device over time (e.g., that have exhibited positive changes in depth across two captured images). In some embodiments, the system can assign a third color or shade (e.g., black) to regions in the ROI that the system determines have not changed in depth toward or away from the image capture device over time (e.g., that have exhibited negligible changes in depth and/or changes in depth equivalent to zero across two images).

In these and other embodiments, the shade and/or intensity (e.g., degree of brightness) of an assigned color can be relative to an amount of excursion of a region in an ROI over time. For example, the shade and/or intensity of an assigned color can be positively correlated with a magnitude of a computed change in depth. In these embodiments, the system (i) can assign a first shade and/or a first intensity of a color (e.g., green) to a first region that the system determines has exhibited a change in depth over time having a first magnitude and (ii) can assign a lighter shade and/or a greater intensity of the color (e.g., green) to a second region that the system determines has exhibited a change in depth over time having a second magnitude greater than the first magnitude. As a result, regions in the ROI with no detected change in depth (e.g., a negligible change in depth and/or a change in depth equivalent to zero) can be displayed as black (e.g., with zero intensity) and/or appear as if no visual indicator has been assigned to these regions.

Regardless of the visual scheme employed, the system can display (e.g., in real-time) the assigned visual indicators over corresponding regions of the ROI in a captured image to visually portray the computed changes in depths. Thus, the assigned visual indicators can exaggerate or emphasize subtle changes in depths detected by the system. In turn, a user (e.g., a caregiver, a clinician, a patient, etc.) can quickly and easily determine whether or not a patient is breathing based on whether or not visual indicators corresponding to one or more breathing cycles of the patient are displayed over the ROI on the patient. As discussed in greater detail below, this can help a user and/or a video-based patient monitoring system to detect a variety of medical conditions, such as apnea, rapid breathing (tachypnea), slow breathing, intermittent or irregular breathing, shallow breathing, and others.

Additionally or alternatively, a user can quickly and easily determine a phase (e.g., inhalation and/or exhalation) of a patient's breathing. For example, a large majority of the ROI 102 in the generated image 461 illustrated in FIG. 4A includes the first pattern 471. As discussed above, the first pattern 471 corresponds to negative changes in depths computed by the system. In other words, the generated image 461 illustrates that the large majority of the ROI 102 is moving toward the image capture device of the system and out from the patient's body over time. Based on this display, a user can quickly and easily determine that the patient is currently inhaling. Similarly, a large majority of the ROI 102 in the generated image 462 illustrated in FIG. 4B includes the second pattern 472. As discussed above, the second pattern 472 corresponds to positive changes in depths computed by the system. In other words, the generated image 462 illustrates that the large majority of the ROI 102 is moving away from the image capture device of the system and in toward the patient's body over time. Based on this display, a user can quickly and easily determine that the patient is currently exhaling.

Figure 5B:
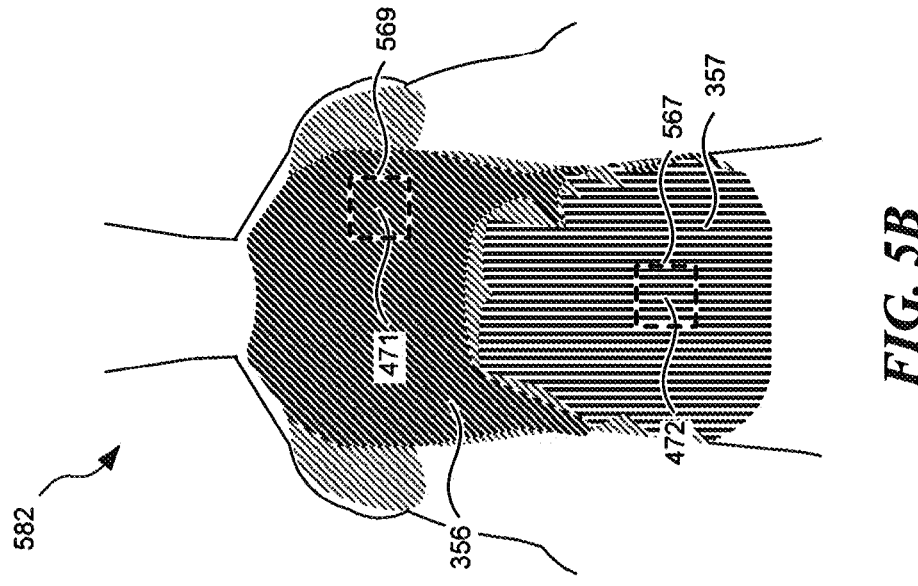
FIGS. 5A-5D are schematic views that illustrate images of regions of interest generated from images captured using an image capture device of a video-based patient monitoring system configured in accordance with various embodiments of the present technology.
Figure 5A:
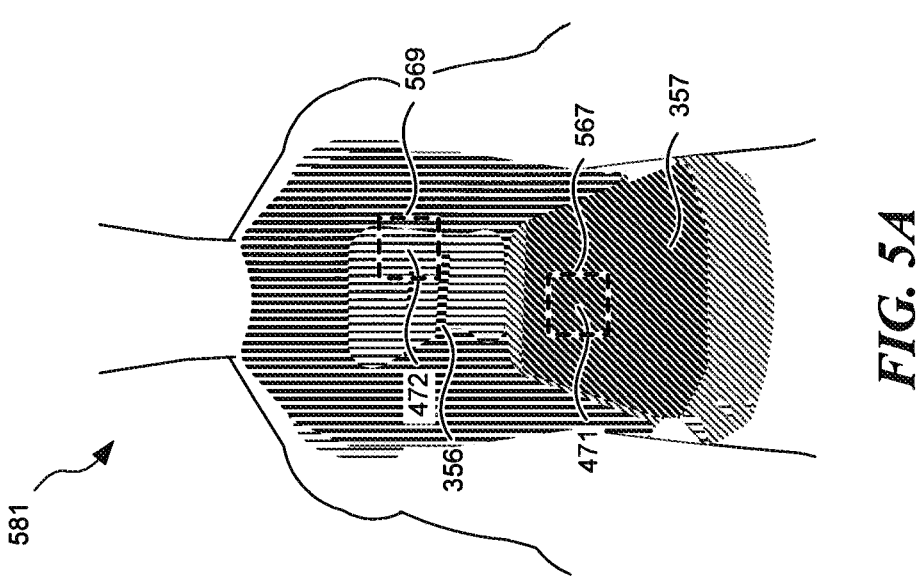

FIGS. 5A-5D are schematic views of images 581-584, respectively, of various regions of interest generated from images captured using an image capture device of a video-based patient monitoring system. As shown in FIG. 5A, the video-based patient monitoring system has defined a ROI 356 corresponding to a patient's chest and a ROI 357 corresponding to the patient's abdomen. The first pattern 471 is displayed over a region 567 of the ROI 357 in the generated image 581. In contrast, the second pattern 472 is displayed over a region 569 of the ROI 356 in the generated image 581. As discussed above, the system can assign the first pattern 471 to a region that exhibits a negative change in depth over time (e.g., that exhibits movement toward the image capture device and/or out from the patient's body across two captured images), whereas the system can assign the second pattern 472 to a region that exhibits a positive change in depth over time (e.g., that exhibits movement away from the image capture device and/or in toward the patient's body across two captured images). Therefore, the generated image 581 illustrates that the region 567 is moving out from the patient's body (e.g., suggesting that the patient is inhaling) while the region 569 is moving in toward the patient's body (e.g., suggesting that the patient is exhaling). In other words, the visual indicators displayed in the image 581 illustrate paradoxical breathing of the patient (e.g., where the chest and the abdomen move out of phase with one another) that can be quickly and easily diagnosed by the system and/or a user monitoring the patient. The generated image 582 illustrated in FIG. 5B similarly depicts paradoxical breathing of the patient but with the chest and abdomen of the patient in opposite phases from the chest and abdomen, respectively, of the patient in the generated image 581 illustrated in FIG. 5A.

Figure 5D:
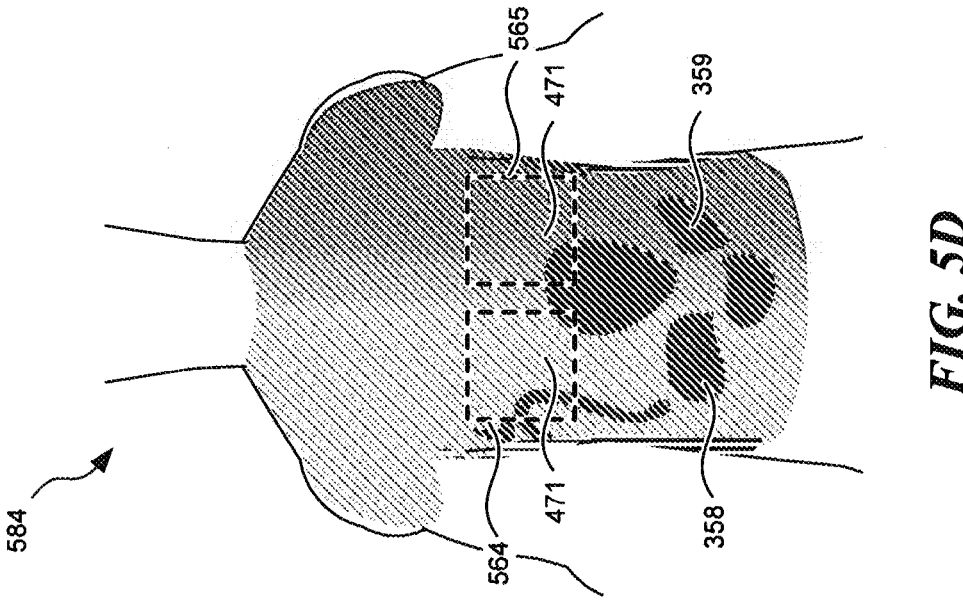
Figure 5C:
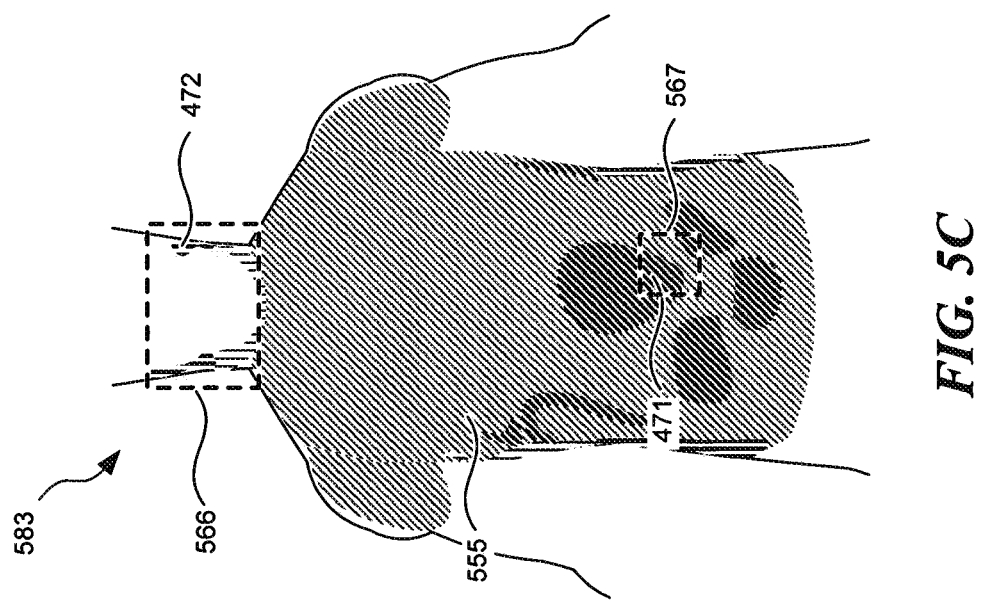

Referring to FIG. 5C, the video-based patient monitoring system has defined an aggregate ROI 555 that includes a patient's torso as well as the patient's neck. The first pattern 471 is displayed over a region 567 of the ROI 555, indicating that the corresponding portion of the patient's body is moving toward the image capture device (e.g., that the patient is inhaling). Nevertheless, the second pattern 472 is displayed over a region 566 of the ROI 555 in the generated image 583 that corresponds to the patient's neck. This suggests that the patient's neck is moving away from the image capture device. In some embodiments, this can indicate (e.g., to the system and/or to a user) that the patient is straining to breathe. In these and other embodiments, the presence of a visual indicator (e.g., above a threshold magnitude) on a patient's neck regardless of the corresponding direction of depth change and/or regardless of whether the direction of the depth change is in sync with the patient's torso can indicate muscle tension associated with the patient straining to breathe. In other words, no visual indicator on the patient's neck or a visual indicator corresponding to a depth change of less than a threshold magnitude can indicate normal breathing and/or that the patient is not straining to breathe.

Referring to FIG. 5D, the video-based patient monitoring system has defined a ROI 358 corresponding to the right half of a patient's torso and a ROI 359 corresponding to the left half of the patient's torso. The first pattern 471 is displayed over regions 564 and 565 of the ROI 358 and 359, respectively, in the generated image 584. The concentration (e.g., the density) of the first pattern 471 displayed over the region 564 of the ROI 358 in the generated image 584, however, is much less than the concentration (e.g., the density) of the first pattern 471 displayed over the region 565 of the ROI 359. As discussed above, the concentration of the first pattern 471 can correspond to (e.g., be positively correlated with) the magnitude of computed depth changes. In other words, the visual indicators displayed in the generated image 584 illustrate that the left half of the patient's torso is exhibiting larger changes in depth as the patient inhales than the right half of the patient's torso. In some embodiments, this can indicate (e.g., to the system and/or to a user) asymmetric breathing across the patient's chest, possibly due to a collapsed lung.

Figures 6A, 6B, 6C:
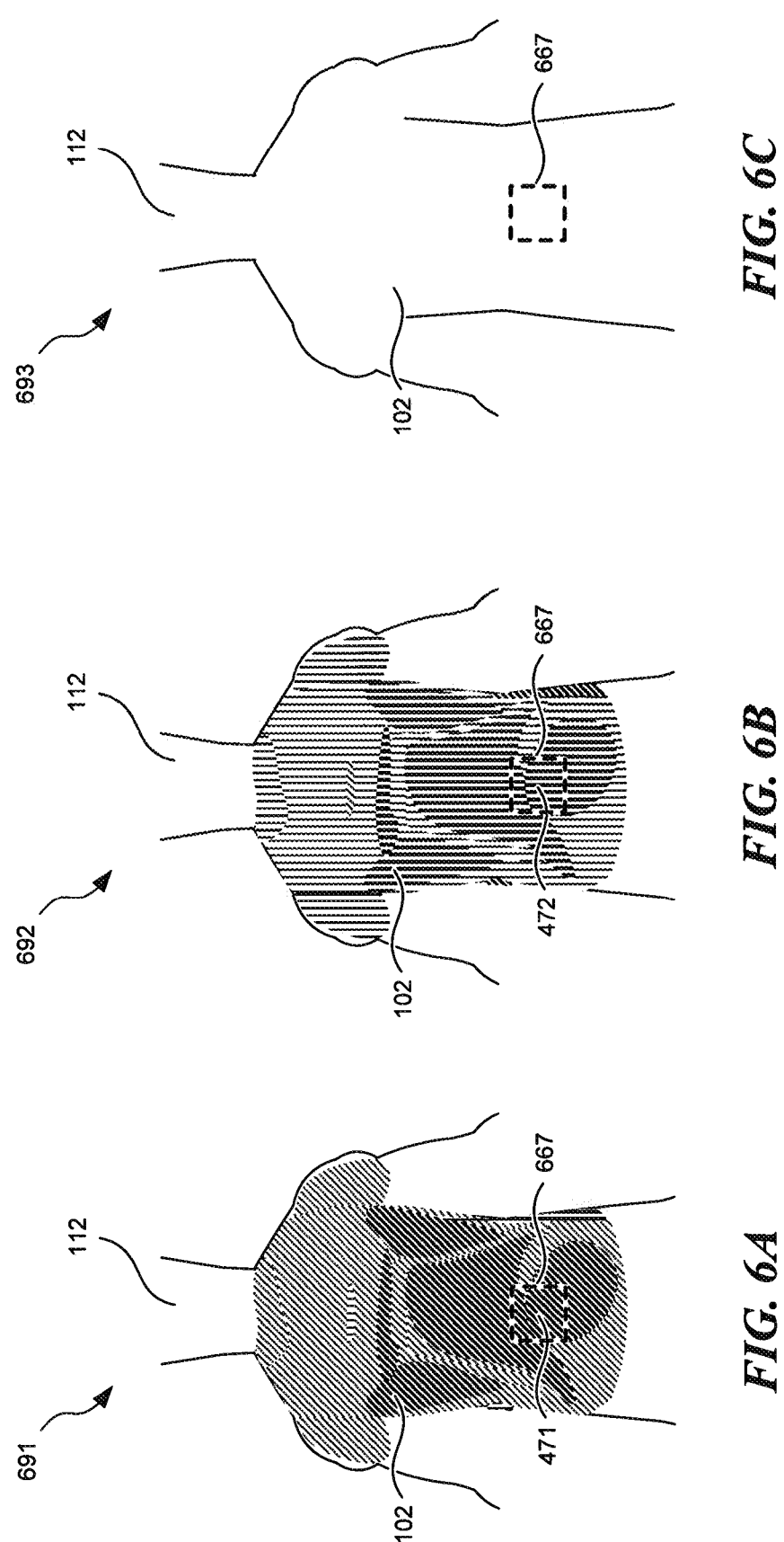
FIGS. 6A-6C are schematic views that illustrate images of a region of interest on a patient generated from images captured using an image capture device of a video-based patient monitoring system configured in accordance with various embodiments of the present technology.

FIGS. 6A-6C are schematic views of generated images 691-693, respectively, of a ROI 102 on a patient 112 facing toward an image capture device of a video-based patient monitoring system. As shown in FIG. 6A, the first pattern 471 is displayed over a region 667 of the ROI 102, indicating that the patient 112 is inhaling in the generated image 691. As shown in FIG. 6B, the second pattern 472 is displayed over the region 667 of the ROI 102, indicating that the patient 112 is exhaling in the generated image 692. The patterns 471 and 472 in the generated images 691 and 692, respectively, are also substantially uniform across the ROI 102. Thus, a user (e.g., a caregiver and/or a clinician) is quickly able to determine that (i) the patient 112 is breathing and (ii) the breathing appears normal in the generated images 691 and 692.

In contrast, the region 667 and other regions of the ROI 102 are displayed in the generated image 693 illustrated in FIG. 6C without the pattern 471 and without the pattern 472. This indicates that no patient breathing is detected in the generated image 693. If a user (e.g., a caregiver and/or a clinician) notices that no patient breathing is detected over one or more (e.g., consecutively) generated images (e.g., including the generated image 693), the user can determine that the patient 112 is not breathing (e.g., is exhibiting apnea) and/or is in need of urgent medical attention.

Figures 7A, 7B, 7C:
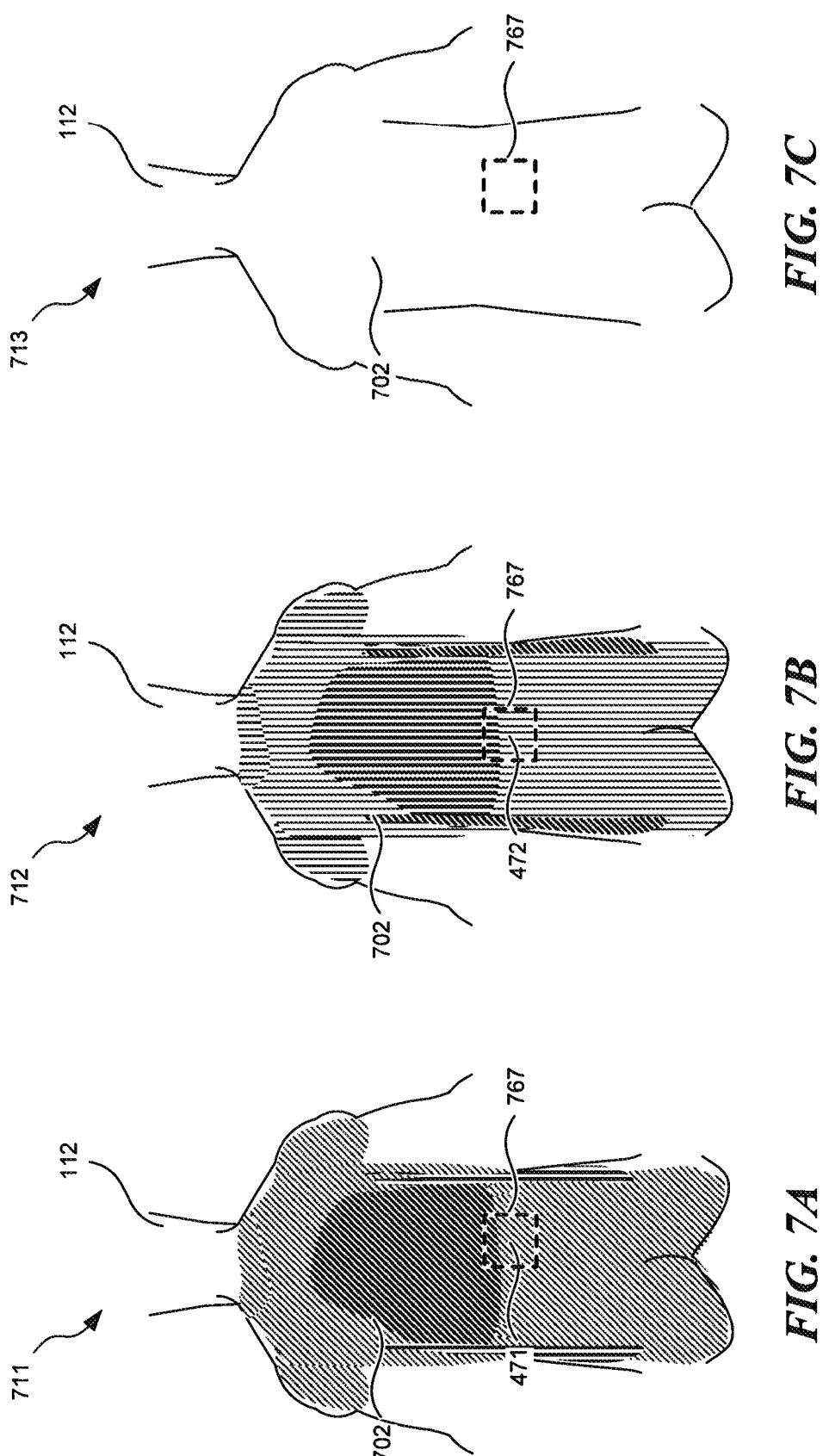
FIGS. 7A-7C are schematic views that illustrate images of a region of interest on a patient generated from images captured using an image capture device of a video-based patient monitoring system configured in accordance with various embodiments of the present technology.

FIGS. 7A-7C are schematic views of generated images 711-713, respectively, of a ROI 702 on a patient 112 facing away from an image capture device of a video-based patient monitoring system. As shown in FIG. 7A, the first pattern 471 is displayed over a region 767 of the ROI 702, indicating that the patient 112 is inhaling in the generated image 711. As shown in FIG. 7B, the second pattern 472 is displayed over the region 767 of the ROI 702, indicating that the patient 112 is exhaling in the generated image 712. Thus, a user (e.g., a caregiver and/or a clinician) is quickly able to determine that (i) the patient 112 is breathing and (ii) the breathing appears normal in the generated images 711 and 712.

In contrast, the region 767 and other regions of the ROI 702 are displayed in the generated image 713 illustrated in FIG. 7C without the pattern 471 and without the pattern 472. This indicates that no patient breathing is detected in the generated image 713. If a user (e.g., a caregiver and/or a clinician) notices that no patient breathing is detected over one or more (e.g., consecutively) generated images (e.g., including the generated image 713), the user can determine that the patient 112 is not breathing (e.g., is exhibiting apnea) and/or is in need of urgent medical attention.

Figure 8C:
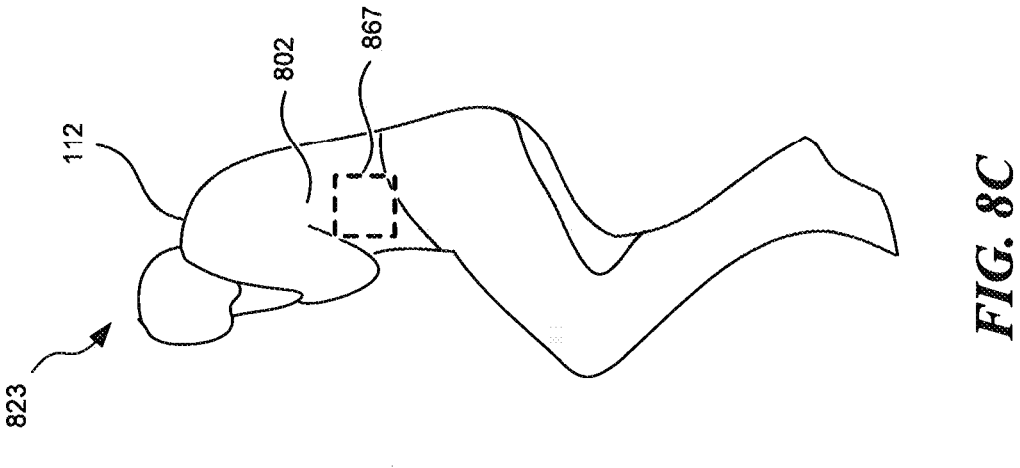
FIGS. 8A-8C are schematic views that illustrate images of a region of interest on a patient generated from images captured using an image capture device of a video-based patient monitoring system configured in accordance with various embodiments of the present technology.
Figure 8B:
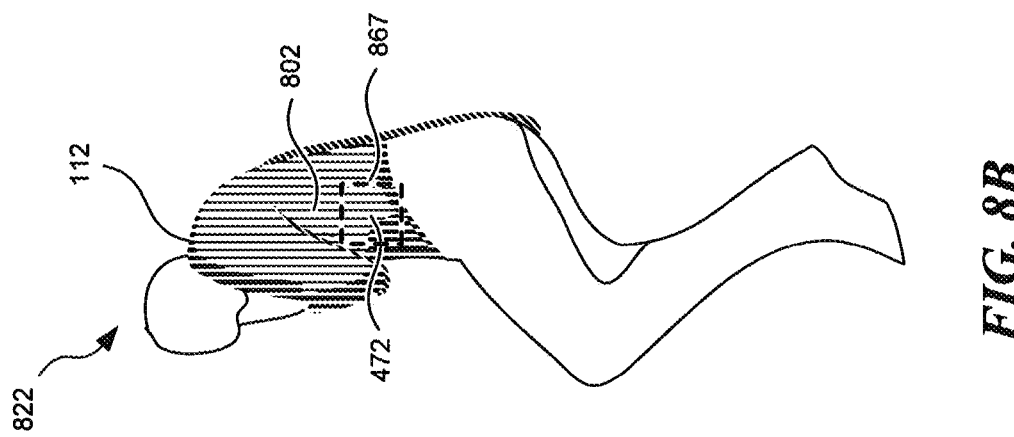
Figure 8A:
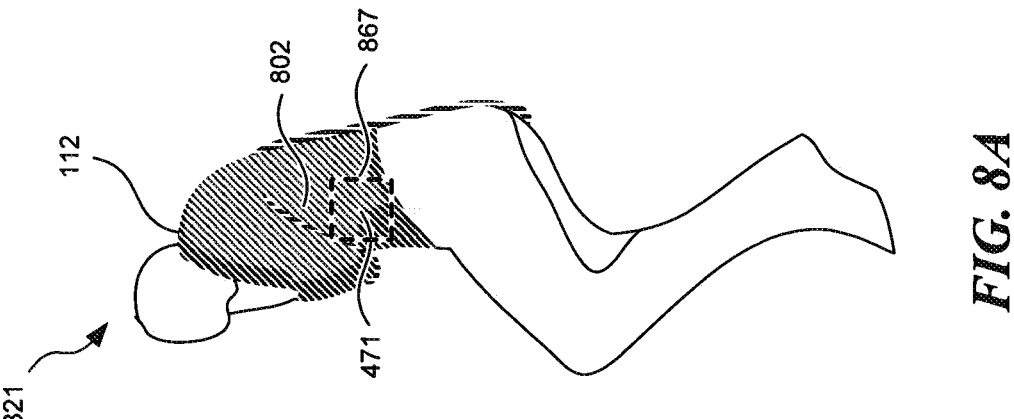

FIGS. 8A-8C are schematic views of generated images 821-823, respectively, of a ROI 802 on a patient 112 on his/her side relative to an image capture device of a video-based patient monitoring system. As shown in FIG. 8A, the first pattern 471 is displayed over a region 867 of the ROI 802, indicating that the patient 112 is inhaling in the generated image 821. As shown in FIG. 8B, the second pattern 472 is displayed over the region 867 of the ROI 802, indicating that the patient 112 is exhaling in the generated image 822. Thus, a user (e.g., a caregiver and/or a clinician) is quickly able to determine that (i) the patient 112 is breathing and (ii) the breathing appears normal in the generated images 821 and 822.

In contrast, the region 867 and other regions of the ROI 802 are displayed in the generated image 823 illustrated in FIG. 8C without the pattern 471 and without the pattern 472. This indicates that no patient breathing is detected in the generated image 823. If a user (e.g., a caregiver and/or a clinician) notices that no patient breathing is detected over one or more (e.g., consecutively) generated images (e.g., including the generated image 823), the user can determine that the patient 112 is not breathing (e.g., is exhibiting apnea) and/or is in need of urgent medical attention.

FIGS. 6A-8C illustrate that video-based patient monitoring systems configured in accordance with embodiments of the present technology can detect and/or monitor patient breathing while a patient is in a variety of orientations with respect to image capture devices of the systems (e.g., when the patient is on his/her back, stomach, and/or side). This can be helpful in determining whether a patient is breathing and/or whether the patient's breathing is abnormal while the patient rests (e.g., at home, in a hospital bed, in a recovery room, in a neonatal ICU, etc.), especially when a patient often changes their orientation and/or when a patient's pulse oximeter and/or other medical sensors become disconnected from the patient.

Additionally or alternatively, the video-based patient monitoring systems can be helpful in determining whether a patient is breathing and/or whether the patient's breathing is abnormal is situations where a patient has fallen. For example, a video-based patient monitoring system can alert a caregiver at a central station (e.g., at a hospital) and/or a caregiver remote from a patient that the patient has fallen. In some embodiments, the caregiver can direct the image capture device toward the fallen patient. In these and other embodiments, the caregiver can view a sequence of generated images on a display screen to determine whether there are cyclical visual indicators (e.g., of a first color and a second color, of a first pattern and a second pattern, etc.) displayed across the sequence of generated images on the patient's torso indicating that the patient is breathing. This can allow the caregiver to quickly determine the urgency of medical attention the patient requires.

Figure 9:
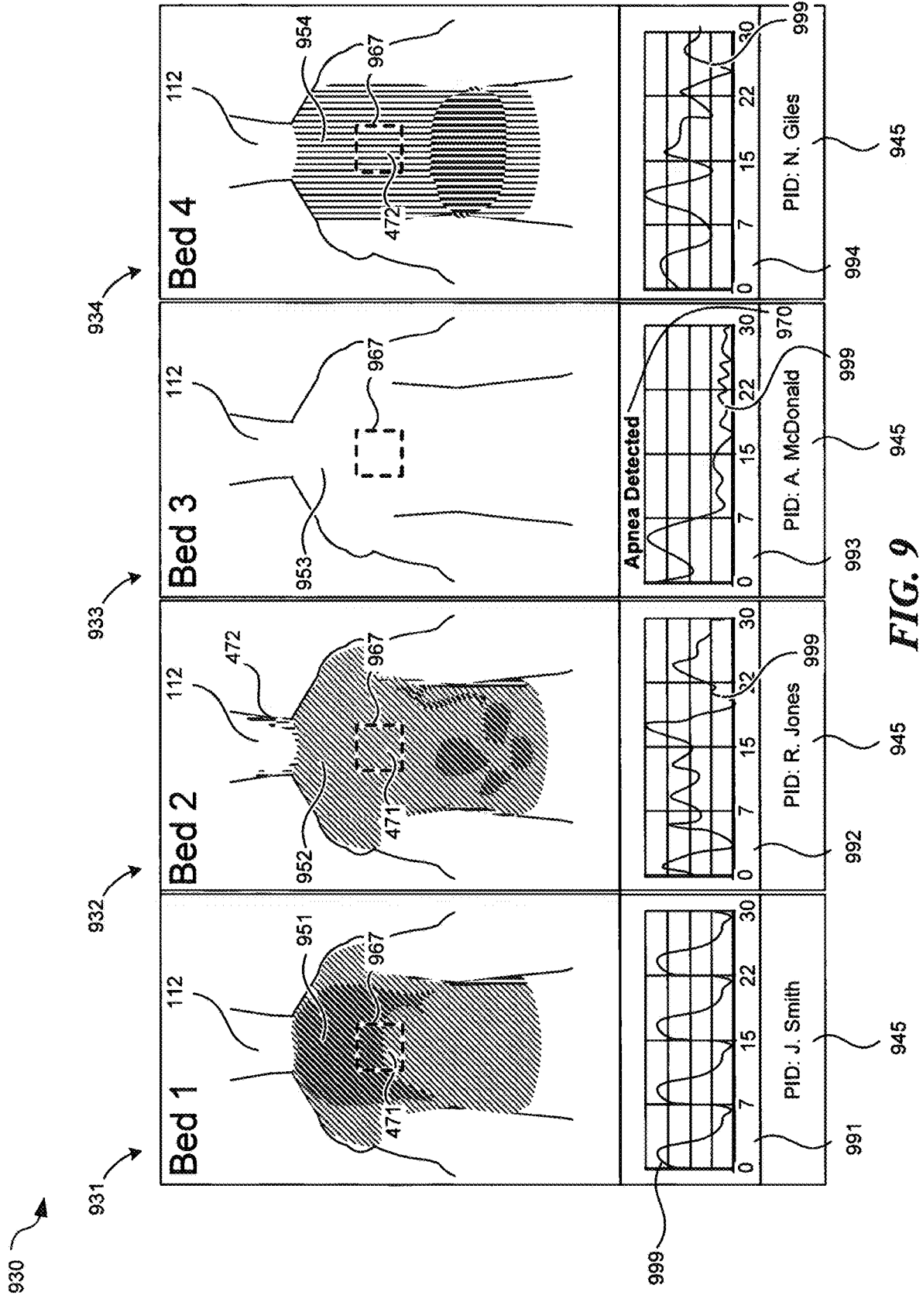
FIG. 9 is a schematic view that illustrates a display of four patients in four images captured and/or generated using video-based patient monitoring systems configured in accordance with various embodiments of the present technology.

FIG. 9 is a schematic view of a display 930 of four patients 112 in four images 931-934 captured and/or generated using video-based patient monitoring systems configured in accordance with various embodiments of the present technology. In some embodiments, the display 930 can be a caregiver's display (e.g., at a central station at a hospital and/or at a remote site from the patients 112). In these and other embodiments, the patients 112 in the generated images 931-934 can be at the same and/or separate locations. For example, one or more of the patients 112 can be in recovery and/or hospital room(s) or can be at their home(s). As shown in FIG. 9, a patient ID 945 for each of the patients 112 can be shown on the display 930 (e.g., to allow a user to quickly determine which patient is portrayed in a given generated image). In some embodiments, a patient ID 945 can be entered for each patient 112 by a user (e.g., the patient, the caregiver, a clinician, etc.) of the systems. In these and other embodiments, the video-based patient monitoring systems can include facial recognition hardware and/or software. As discussed in greater detail below, the systems can recognize the patients 112 by recognizing one or more characteristics of the patients' faces. Once the systems recognize the patients 112, the systems can automatically populate the patient ID 945 on the display 930 for each patient 112.

As shown in FIG. 9, a user (e.g., a caregiver, a clinician, etc.) of the system viewing (e.g., monitoring) the display 930 can quickly determine whether or not any given patient 112 is breathing and/or whether that patient's breathing is abnormal. Referring to the generated image 931, for example, the user can quickly determine that the patient 112 is inhaling (e.g., based on the display of the first pattern 471 over a region 967 and other regions of a ROI 951 in the generated image 931). Similarly, a line plot 992 of a tidal volume signal 999 can be displayed beneath the generated image 931 on the display 930 to provide an indication of the patient's tidal volume over time. As described in greater detail below, the tidal volume signal 999 can be used to determine one or more abnormalities in the patient's breathing.

Referring to the generated image 932, the user can similarly determine that the patient 112 is inhaling (e.g., based on the display of the first pattern 471 over a region 967 and other regions of a ROI 952 in the generated image 932). In contrast with the patient 112 portrayed in the generated image 931, however, the patient 112 in the generated image 932 is straining to breath, which is evidenced by the display of the second pattern 472 on the patient's neck. Additionally a tidal volume signal 999 displayed in a line plot 992 beneath the patient 112 on the display 930 includes erratic amplitudes, illustrating that the patient 112 in the generated image 932 is rapidly and/or erratically breathing, which indicates that the patient is having difficulty breathing. The line plot 992 can be used in addition to or alternatively to the generated image 932, to show the patient's status.

Referring to the generated image 933, the user can quickly determine that no patient breathing is detected in the generated image 933 (e.g., based on the lack of the first pattern 471 and the second pattern 472 shown over a region 967 and other regions of a ROI 953 in the generated image 933). In some embodiments, the user can confirm that the patient 112 is not breathing by monitoring one or more (e.g., consecutively) generated images (e.g., including the generated image 933) and seeing that no patient breathing is detected across the one or more generated images. In these and other embodiments, the user can confirm that the patient 112 is not breathing by analyzing a tidal volume signal 999 displayed in a line plot 993 beneath the patient 112 on the display 930. As shown, the tidal volume signal 999 in the plot 993 is relatively flat for the past 22.5 seconds, suggesting that the patient 112 has not been breathing for approximately that period of time.

As described in greater detail below, the system can additionally or alternatively analyze the tidal volume signal 999 and/or other breathing parameter signals to determine whether a patient 112 is exhibiting breathing abnormalities. In some embodiments, if the system detects a breathing abnormality, the system can trigger an audio and/or visual alarm to alert a user (e.g., the patient, the caregiver, the clinician, etc.). In the embodiment illustrated in FIG. 9, for example, the system has triggered a visual alarm 970 to alert a user that the patient 112 in the generated image 933 is exhibiting signs of apnea.

Referring to the generated image 934, the user can quickly determine that the patient 112 is exhaling (e.g., based on the display of the second pattern 472 over a region 967 and other regions of a ROI 954 in the generated image 934). Similarly, a line plot 994 of a tidal volume signal 999 can be displayed beneath the generated image 934 on the display 930 to provide an indication of the patient's tidal volume over time. The tidal volume signal 999 in the plot 994 is substantially similar to the tidal volume signal 999 in the plot 991, and both of these tidal volume signals 999 illustrate normal, healthy breathing with respect to tidal volume.

Figures 10A, 10B:
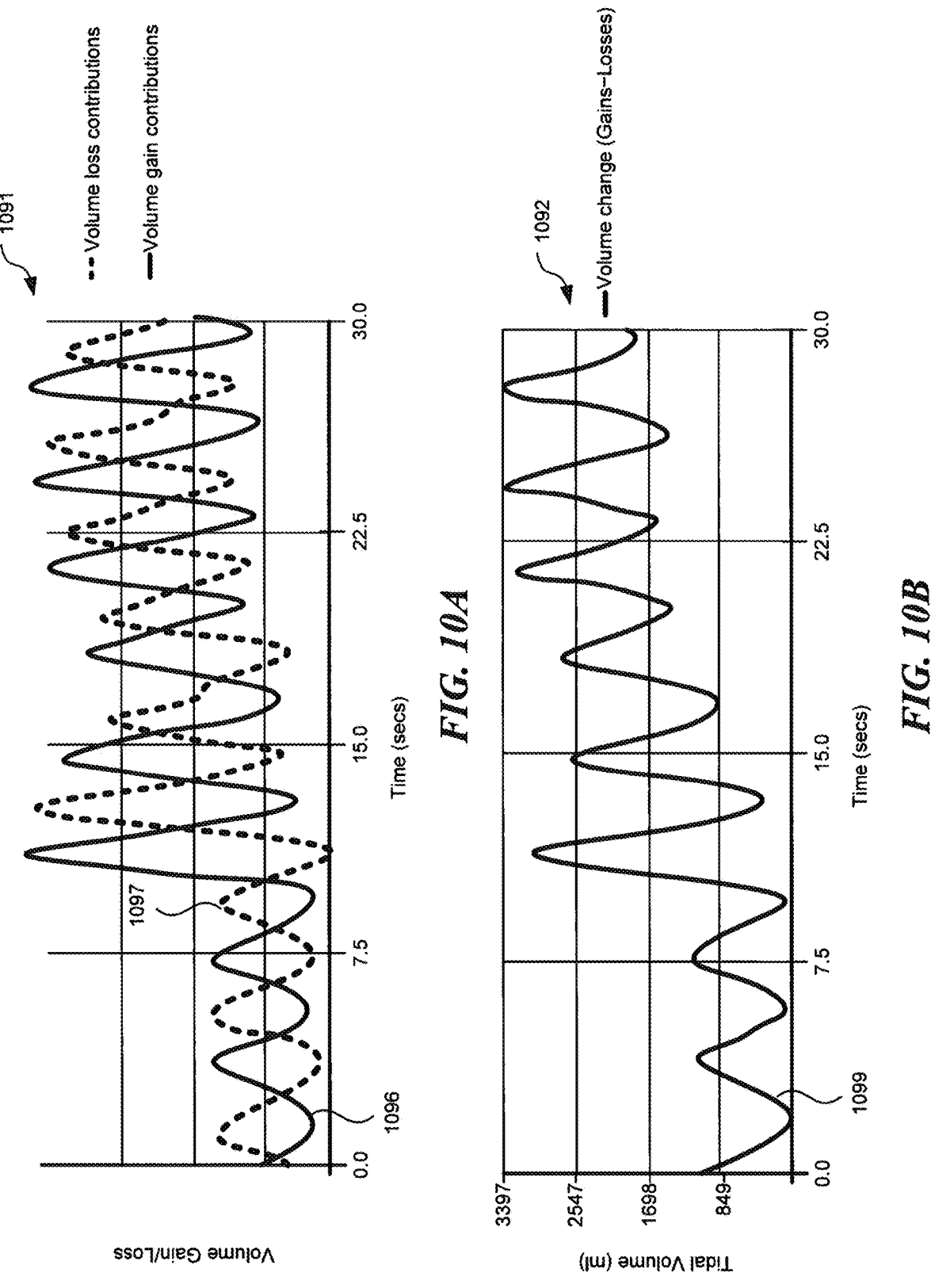
FIG. 10A is a line plot that illustrates a volume gain signal and a volume loss signal in a region of interest over time and generated using a video-based patient monitoring system configured in accordance with various embodiments of the present technology.
FIG. 10B is a line plot that illustrates a tidal volume signal in a region of interest over time and generated using a video-based patient monitoring system configured in accordance with various embodiments of the present technology.

FIG. 10A is a line plot 1091 illustrating a volume gain signal 1096 and a volume loss signal 1097 in a region of interest (e.g., ROI 102 shown in FIGS. 1, 3, 4A and 4B) over time and generated using a video-based patient monitoring system configured in accordance with various embodiments of the present technology. In some embodiments, the system (i) can generate the volume gain signal 1096 by (e.g., continuously) integrating (e.g., summing up) all volume increases in the ROI and/or (ii) can generate the volume loss signal 1097 by (e.g., continuously) integrating (e.g., summing up) all volume decreases in the ROI. Volume increases can correspond to negative changes in depth computed by the system (e.g., to regions of the ROI moving toward the image capture device), whereas volume decreases can correspond to positive changes in depth computed by the system (e.g., to regions of the ROI moving away from the image capture device).

In some embodiments, the video-based patient monitoring system can use the volume gain signal 1096 and/or the volume loss signal to determine one or more parameters of a patient's breathing. As shown in FIG. 10A, for example, the volume gain signal 1096 is approximately 180 degrees out of phase with the volume loss signal 1097. In other words, the volume gain signal 1096 and the volume loss signal 1097 in the plot 1091 illustrate that the patient is breathing normally. As the patient inhales, the volume gain (e.g., the sum of the magnitudes of all negative changes in depths computed by the system) in the ROI increases while the volume loss (e.g., the sum of the magnitudes of all positive changes in depths computed by the system) in the ROI decreases, and vice versa.

In contrast, when a patient exhibits abnormal breathing behaviors, the phase difference between the volume gain signal 1096 and the volume loss signal 1097 changes markedly away from the approximate 180-degree phase difference observed under normal breathing. For example, when a patient exhibits paradoxical breathing (as shown in FIGS. 5A and 5B), the phase of the volume gain signal 1096 and will be much closer to the phase of the volume loss signal 1097 (e.g., the phase difference between the volume gain signal 1096 and the volume loss signal 1097 will move closer to zero degrees). As such, the system and/or a user can detect paradoxical breathing in a patient by monitoring the volume gain signal 1096 and the volume loss signal 1097 and/or can trigger an alert and/or alarm when the volume gain signal and the volume loss signal change more than a threshold value away from the 180-degree phase difference.

FIG. 10B is a line plot 1092 illustrating a tidal volume signal 1099 in a region of interest (e.g., ROI 102 shown in FIGS. 3, 4A, and 4B) over time and generated using a video-based patient monitoring system configured in accordance with various embodiments of the present technology. The tidal volume signal 1099 corresponds to the volume gain signal 1096 and the volume loss signal 1097 illustrated in the plot 1091 shown in FIG. 10A. In some embodiments, the system can generate the tidal volume signal 1099 by (e.g., continuously) integrating all volume changes computed across the ROI and/or by subtracting the volume loss signal 1097 from the volume gain signal 1096. The tidal volume signal 1099 can provide an indication of the normal volume of air displaced by a patient between normal inhalation and exhalation.

In some embodiments, the video-based patient monitoring system can use the tidal volume signal 1099 to determine one or more parameters of a patient's breathing. For example, a patient's respiratory rate can be calculated by determining the period of the tidal volume signal 1099. In these and other embodiments, assuming that (i) a trough represented on the tidal volume signal 1099 corresponds to a patient's maximum exhalation and (ii) a peak represented on the tidal volume signal 1099 corresponds to the patient's maximum inhalation, the patient's inhalation tidal volume can be calculated by taking a trough to peak measurement of the tidal volume signal 1099 corresponding to a single breath of the patient. Additionally, or alternatively, a patient's exhalation tidal volume can be calculated by taking a peak to trough measurement of the tidal volume signal 1099 corresponding to a single breath of the patient. In embodiments where the tidal volume signal 1099 is displayed inverted, a peak to trough measurement of a single breath of a patient can determine the patient's inhalation tidal volume, whereas a trough to peak measurement of a single breath of the patient can determine the patient's exhalation tidal volume. These measurements taken over a minute can be used to calculate the patient's inhalation and/or exhalation minute volumes (e.g., by summing the patient's corresponding tidal volume measurements over the span of a minute, by multiplying the patient's corresponding tidal volume and the patient's respiratory rate, etc.).

In these and other embodiments, the video-based patient monitoring system can use the tidal volume signal 1099 as an indicator of other breathing characteristics. For example, when the tidal volume signal 1099 indicates that the patient is displacing a small volume of air between inhalation and exhalation (e.g., a negligible volume of air, a volume of air equivalent to zero, a volume of air less than a predetermined threshold volume of air and/or below a predetermined tidal volume range, etc.), the system (and/or a clinician) can determine that the patient is either not breathing and/or that the patient's breathing is restricted and/or impaired. In these and other embodiments, when the tidal volume signal 1099 indicates that the patient is displacing a large volume of air between inhalation and exhalation (e.g., a volume of air greater than a predetermined threshold volume of air and/or above a predetermined tidal volume range), the system (and/or a clinician) can determine that the patient (i) is at risk of lung injury or trauma and/or (ii) is in respiratory distress, trauma, or pain. The can be useful, for example, when a mechanical ventilator is connected to the patient. In these and still other embodiments, the system can calculate a degree of consistency in the volume of air in each breath from the tidal volume signal and/or can display the computed consistency/consistencies (e.g., to a clinician) to illustrate the variability in tidal volume over a period of time. In these and still other embodiments, the system can compute an inhalation to exhalation ratio (I/E ratio) from the tidal volume signal and/or can display the I/E ratio to a user. As described in greater detail below, the system can trigger an alert and/or an alarm when the tidal volume, the I/E ratio, and/or the degree of consistency are/move outside of one or more predetermined ranges and/or above or below one or more threshold values.

The generated I/E ratio and/or the generated tidal volume signal 1099 can also be useful in other applications. For example, an amount of carbon dioxide a patient exhales and/or a patient's pulse oximetry signal are often used to monitor the patient's respiration. As specific examples, a decline in the amount of carbon dioxide a patient exhales (e.g., indicated by a capnography waveform) and/or a decline in the patient's peripheral pulse oxygen saturation (e.g., the patient's SpO2 or pulse oximetry signal) can often be used as early indications of respiratory compromise. In high flow oxygen therapy, however, a high flow rate of oxygen is provided to the patient that washes out carbon dioxide the patient exhales, making it difficult to accurately determine the amount of carbon dioxide exhaled by the patient. Additionally, or alternatively, when the patient is experiencing respiratory compromise, the flow of oxygen in high flow oxygen therapy can delay and/or impair a noticeable decline in the pulse oximetry signal (e.g., the flow of oxygen can keep the oxygen saturation artificially high). As such, monitoring (i) the amount of carbon dioxide the patient exhales and/or (ii) the patient's oxygen saturation for early indications of respiratory compromise can be ineffective during high flow oxygen therapy and similar settings. The patient's tidal volume signal 1099 generated in accordance with embodiments of the present technology, however, remains useful in these settings. Thus, a decline in the patient's generated tidal volume signal 1099 can be used as an early indication of respiratory compromise (and ultimately respiratory arrest) in the high flow therapy context.

As additional examples, the generated I/E ratio and/or the generated tidal volume signal 1099 can be used to detect talking and/or coughing. Talking involves a large amount of exhalation followed by a quick inhalation, which can be visualized and/or detected in the generated tidal volume signal 1099. Similarly, coughing appears and/or can be detected as localized impulses or peaks over short time scales on the generated tidal volume signal 1099. In these and other embodiments, the system can use the generated tidal volume signal 1099 and/or other generated signals (e.g., a trending minute volume signal, a respiratory rate signal, an absolute minute volume signal, an absolute tidal volume signal, etc.) derived from the change in depth information to determine other parameters of patient breathing. For example, the generated tidal volume signal 1099 and/or a generated respiratory rate signal can be used to determine when a patient is hyperventilating, is not breathing, and/or is exhibiting apnea.

In some embodiments, a video-based patient monitoring system can generate more than one volume gain signal, volume loss signal, and/or tidal volume signal. For example, the system can define two ROI's (e.g. the ROI 356 and the ROI 357 shown in FIG. 3) where one ROI corresponds to a patient's chest and the other ROI corresponds to patient's abdomen. In these embodiments, the system can calculate a volume gain signal and a volume loss signal for each ROI. When the volume gain signal of one ROI has the same phase as the volume gain signal of the other ROI, the system can determine that the patient's chest and abdomen are in phase (e.g., that the patient is breathing normally and/or is not exhibiting paradoxical breathing). On the other hand, when the volume gain signal of one ROI is substantially out of phase (e.g., 45 degrees out of phase, 90 degrees out of phase, 180 degrees out of phase, etc.) with the volume gain signal of the other ROI, the system can determine that the patient is exhibiting paradoxical breathing as illustrated in FIGS. 5A and 5B. The system can perform a similar analysis using the volume loss signal and/or a tidal volume signal generated for one ROI in comparison with the volume loss signal and/or a tidal volume signal, respectively, generated for the other ROI. In some embodiments, the system can trigger an alert and/or an alarm when the system detects paradoxical breathing.

In these and other embodiments, the system can define two ROI's (e.g. the ROI 358 and the ROI 359 shown in FIG. 3) where one ROI corresponds to the right half of a patient's chest or torso and the other ROI corresponds to left half of the patient's chest or torso. In these embodiments, the system can calculate a volume gain signal and a volume loss signal for each ROI. When the volume gain signal of one ROI is substantially out of phase (e.g., 90 or 180 degrees out of phase) with the volume gain signal of the other ROI and/or when the volume gain signal of the one ROI is exhibiting an amplitude significantly less than the amplitude of the volume gain signal of the other ROI, the system can determine that the patient is exhibiting abnormal breathing across the patient's chest (e.g., due to a collapsed lung), as illustrated in FIG. 5D. The system can perform a similar analysis using the volume loss signal and/or a tidal volume signal generated for one ROI in comparison with the volume loss signal and/or a tidal volume signal, respectively, generated for the other ROI. In some embodiments the system can trigger an alert and/or alarm when the system detects abnormal breathing across ROI's.

Figure 11:
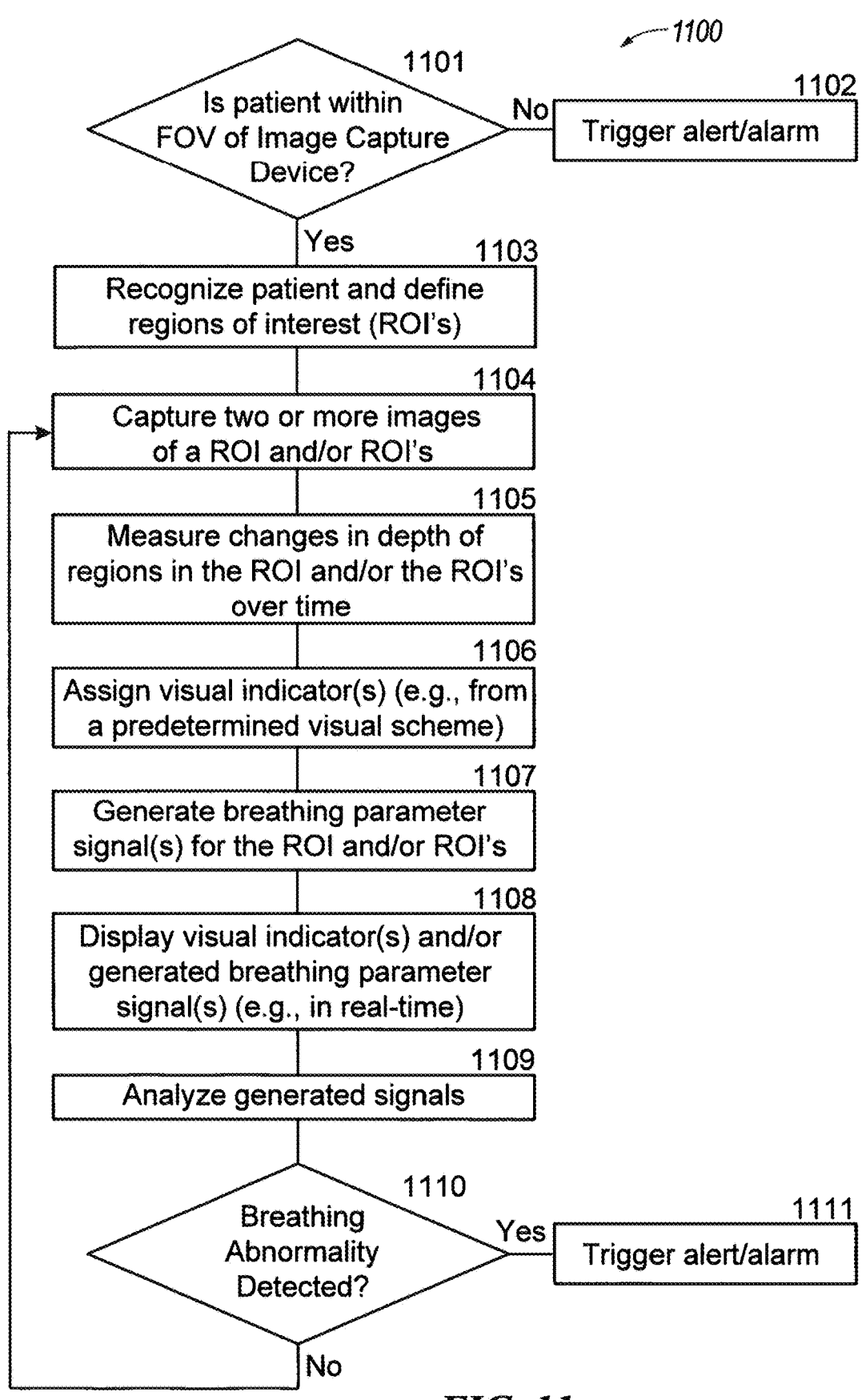
FIG. 11 is a flow diagram that illustrates a video-based patient monitoring routine of a method for detecting and monitoring breathing in a patient in accordance with various embodiments of the present technology.

FIG. 11 is a flow diagram illustrating a video-based patient monitoring routine 1100 of a method for detecting and monitoring breathing in a patient in accordance with various embodiments of the present technology. All or a subset of the steps of the routine 1100 can be executed by various components of a video-based patient monitoring system and/or a user of the system (e.g., a caregiver, a clinician, a patient, etc.). For example, all or a subset of the steps of the routine 1100 can be executed by (i) components of the video-based patient monitoring system 100 shown in FIG. 1 and/or (ii) components of the video-based patient monitoring system 200 shown in FIG. 2.

The routine 1100 can begin at block 1101 by determining whether a patient is within a field of view FOV of an image capture device of the video-based patient monitoring system. In some embodiments, the routine 1100 can direct the image capture device toward a patient bed (e.g., in a hospital room, at home, etc.), and the routine 1100 can determine whether a patient is within the bed by determining whether the patient is within the FOV of the image capture device. In these and other embodiments, the routine 1100 can direct the image capture device toward the patient (e.g., to monitor a patient that has moved and/or fallen out of the FOV of the image capture device). If the routine 1100 determines that a patient is not within the FOV of the image capture device, the routine 1100 can proceed to block 1102 to trigger an alert or alarm. On the other hand, if the routine 1100 determines that a patient is within the FOV of the image capture device, the routine 1100 can proceed to block 1103 to recognize the patient and/or to define one or more regions of interest (ROI's) on the patient.

At block 1102, the routine 1100 triggers an alert and/or an alarm. In some embodiments, the alert or alarm can be an audio alert or alarm to, for example, alert a clinician and/or the patient that the patient has moved and/or fallen outside of the FOV of the image capture device. In these and other embodiments, the routine 1100 can trigger a visual alert or alarm on a display. For example, the routine 1100 can display a visual alert or alarm (e.g., notification) on a display to notify a user (e.g., during set up) that the routine 1100 does not recognize a patient in the FOV of the image capture device and/or that user input is required. As another example, the routine 1100 can display a visual alert or alarm (e.g., a notification) on a display of a caregiver at a central station in a hospital and/or at a remote site. The visual alert or alarm can notify the caregiver that a patient has moved and/or fallen out of the FOV of the image capture device. This can enable the caregiver (i) to redirect the image capture device toward the patient and/or (ii) to determine whether or not the patient is breathing and/or the state of the patient's breathing (e.g., to assess the urgency of medical attention required). Additionally or alternatively, the routine 1100 can trigger an alert or alarm on a display visible to the patient to notify the patient that the patient has moved outside of the FOV of the image capture device (e.g., during a medical exam and/or other monitoring). In these and still other embodiments, the routine 1100 can trigger an alert and/or alarm unique to the routine 1100 determining a patient is not within the FOV of the image capture device (e.g., an alert and/or alarm different from other alerts and/or alarms the routine 1100 can trigger at block 1111, discussed in greater detail below). In other embodiments, the routine 1100 can trigger a same alert and/or alarm as an alert and/or alarm triggered at block 1111, discussed in greater detail below.

At block 1103, the routine 1100 recognizes a patient within the FOV of the image capture device and/or defines one or more regions of interest (ROI's) on the patient. In some embodiments, the routine 1100 can recognize the patient by identifying the patient using facial recognition hardware and/or software of the image capture device. In these embodiments, the routine 1100 can display the name of the patient on a display screen once the routine 1100 has identified the patient. In these and other embodiments, the routine 1100 can recognize a patient within the FOV of the image capture device by determining a skeleton outline of the patient and/or by recognizing one or more characteristic features (e.g., a torso of a patient). In these and still other embodiments, the routine 1100 can define one or more ROI's on the patient in accordance with the discussion above with respect to FIGS. 1 and/or 3. For example, the routine 1100 can define one or more ROI's on the patient using extrapolation from a point on the patient, using inferred positioning from proportional and/or spatial relationships with the patient's face, using parts of the patient having similar depths from the camera 114 as a point, using one or more features on the patient's clothing, using user input, etc.

At block 1104, the routine 1100 captures two or more images of one or more ROI's. In some embodiments, the routine 1100 can capture the two or more images of the one or more ROI's by capturing a video sequence of the one or more ROI's. In these and other embodiments, the routine 1100 can capture the two or more images of the one or more ROI's by capturing separate still images of the one or more ROI's. The routine 1100 can capture the two or more still images at a rate faster than a period of the patient's respiration cycle to ensure that the two or more still images occur within one period of the patient's respiration cycle.

At block 1105, the routine 1100 can measure changes in depth of one or more regions in one or more ROI's over time. In some embodiments, the routine 1100 can measure changes in depth of regions in the one or more ROI's in accordance with the discussion above with respect to FIGS. 4A-9. For example, the routine 1100 can measure a change in depth by computing a difference between a depth of a region of a ROI in a first captured image of the ROI and a depth of the same region in a second captured image of the ROI.

At block 1106, the routine 1100 can assign one or more visual indicators to one or more regions in the ROI. In some embodiments, the one or more visual indicators can be colors, patterns, shades, concentrations, intensities, etc. In these and other embodiments, the routine 1100 can assign the one or more visual indicators in accordance with a predetermined visual scheme. In these and still other embodiments, the routine 1100 can assign one or more visual indicators to one or more regions in accordance with the discussion above with respect to FIGS. 4A-9. For example, the routine 1100 can assign one or more visual indicators to the one or more regions based at least in part on the (e.g., sign and/or magnitude of a) measured/computed change in depth exhibited by a region over time (e.g., across two captured images of the ROI).

At block 1107, the routine 1100 generates one or more breathing parameter signals. In some embodiments, the routine 1100 generates a volume gain signal and/or a volume loss signal for one or more ROI's in accordance with the discussion above with respect to FIGS. 10A and/or 10B. In these and other embodiments, the routine 1100 generates a tidal volume signal for one or more ROI's in accordance with the discussion above with respect to FIGS. 10A and/or 10B. In these and still other embodiments, the routine 1100 generates one or more other breathing parameter signals for one or more ROI's. For example, the routine 1100 can generate an inhalation-to-exhalation ratio for one or more ROI's, a degree of consistency value indicating consistency in the volume of each breath for one or more ROI's, a trending and/or an absolute minute volume signal for one or more ROI's, a respiratory rate signal for one or more ROI's, a SpO2 signal for one or more ROI's, and/or an absolute tidal volume signal for one or more ROI's, among others.

At block 1108, the routine 1100 displays one or more visual indicators assigned at block 1106 over corresponding regions of one or more ROI's and/or displays one or more of the breathing parameter signals generated at block 1107. In some embodiments, the routine 1100 can display the one or more visual indicators in accordance with the discussion above with respect to FIGS. 4A-9. For example, the routine 1100 can display the one or more visual indicators over a corresponding region in a corresponding ROI (e.g., over a corresponding portion of the patient). In these and other embodiments, the routine 1100 can display a generated volume gain signal, a generated volume loss signal, a generated trending tidal volume signal, a generated absolute tidal volume signal, a generated trending minute volume signal, a generated absolute minute volume signal, a generated respiratory rate signal, a generated inhalation-to-exhalation ratio, a generated degree of consistency in the volume of each breath, and/or a generated SpO2 signal for one or more ROI's. In these and still other embodiments, the one or more visual indicators and/or one or more of the generated breathing parameter signals can be displayed in real-time. In these and other embodiments, the one or more visual indicators and/or one or more of the generated breathing parameter signals can be recorded such that they can be displayed at a later time (e.g., for a clinician to review). In these and still other embodiments, the one or more visual indicators and/or one or more of the breathing parameter signals can be displayed on a clinician's display, on a caregiver's display, and/or on a patient's display. For example, the one or more visual indicators and/or one or more of the breathing parameter signals can be displayed on a caregiver's display where the display is at a central station (e.g., in a hospital) and/or at a remote site from the patient.

At block 1109, the routine 1100 analyzes one or more of the breathing parameter signals generated at block 1107 to determine whether a patient is exhibiting one or more breathing abnormalities. In some embodiments, the routine 1100 can analyze one or more of the breathing parameter signals generated at block 1107 in accordance with the discussion above with respect to FIGS. 10A and/or 10B. For example, the routine 1100 can analyze a generated volume gain signal and a generated volume loss signal corresponding to a ROI. If the volume gain signal is not approximately 180 degrees out of phase with the volume loss signal, the routine 1100 can determine that the patient is exhibiting a breathing abnormality. In the event the routine 1100 determines that the volume gain signal is substantially in phase with the volume loss signal, the routine 1100 can determine that the patient is exhibiting paradoxical breathing.

In these and other embodiments, the routine 1100 can analyze a generated volume gain signal for a first ROI corresponding to a patient's chest and a generated volume gain signal for a second ROI corresponding to the patient's abdomen. If the volume gain signals are substantially out of phase (e.g., 45 degrees out of phase, 90 degrees out of phase, 180 degrees out of phase, etc.) with one another, the routine 1100 can determine that the patient is exhibiting paradoxical breathing. In some embodiments, the routine 1100 can perform a similar analysis with (i) a generated volume loss signal and/or a generated tidal volume signal of the first ROI and (ii) a generated volume loss signal and/or a generated tidal volume signal, respectively, of the second ROI.

In these and still other embodiments, the routine 1100 can analyze a generated volume gain signal for a first ROI corresponding to the right side of a patient's chest and/or torso and a generated volume gain signal for a second ROI corresponding to the left side of the patient's chest and/or torso. If (i) the volume gain signal of the first ROI is substantially out of phase (e.g., 90 or 180 degrees out of phase) with the volume gain signal of the second ROI and/or (ii) the volume gain signal of the first ROI is exhibiting an amplitude significantly less than the amplitude of the volume gain signal of the second ROI, the routine 1100 can determine that the patient is exhibiting abnormal breathing across the patient's chest (e.g., due to a collapsed lung), as illustrated in FIG. 5D. In some embodiments, the routine 1100 can perform a similar analysis with a volume loss signal generated for the first ROI and a volume loss signal generated for the second ROI.

In these and other embodiments, the routine 1100 can analyze a tidal volume signal generated for a ROI. In some embodiments, the routine 1100 can predetermine a tidal volume range (e.g., using a low threshold tidal volume value and a high threshold tidal volume value). The predetermined tidal volume range can be dependent upon a patient's characteristics (e.g., height, weight, gender, etc.). If a tidal volume for the patient falls outside of (e.g., above and/or below) the predetermined tidal volume range, the routine 1100 can determine that the patient is exhibiting a breathing abnormality. For example, if the tidal volume for the patient is and/or drops below a low tidal volume threshold value of the predetermined tidal volume range, the routine 1100 can determine that the patient is not breathing and/or that the patient's breathing is restricted and/or impaired. In these and other embodiments, if the tidal volume for the patient is and/or rises above the high tidal volume threshold value of the predetermined tidal volume range, the routine 1100 can determine that the patient (i) is at risk of lung injury or trauma (e.g., if connected to a mechanical ventilator) and/or (ii) is in respiratory distress, trauma, or pain.

In some embodiments, the routine 1100 can perform a similar analysis with (i) a generated inhalation-to-exhalation ratio and a predetermined inhalation-to-exhalation ratio range and/or threshold values, (ii) a generated degree of consistency in the volume of each breath and a predetermined degree of consistency range and/or threshold values, (iii) a generated volume gain signal and a predetermined volume gain range and/or threshold values, (iv) a generated volume loss signal and a predetermined volume loss range and/or threshold values, (v) a generated trending and/or absolute minute volume signal and a predetermined minute volume range and/or threshold values, (vi) a general absolute tidal volume signal and a predetermined absolute volume range and/or threshold values, (vii) a generated respiratory rate signal and a predetermined respiratory rate range and/or threshold values, and/or (viii) a generated SpO2 signal and a predetermined SpO2 range and/or threshold values, among others. For example, if a patient's respiratory rate is and/or drops below a predetermined respiratory rate threshold value and/or range, the routine 1100 can determine that the patient is not breathing, that the patient is exhibiting apnea, and/or that the patient's breathing is restricted and/or impaired. In these and other embodiments, if a patient's respiratory rate is and/or rises above a predetermined respiratory rate threshold value and/or range, the routine 1100 can determine that the patient is hyperventilating and/or is in respiratory distress, trauma, or pain.

In these and still other embodiments, the routine 1100 can analyze other information and/or signals generated and/or displayed by the routine 1100 at blocks 1105, 1106, 1107, and/or 1108. For example, the routine can analyze the I/E ratio and/or the tidal volume signal corresponding to a ROI to detect talking and/or coughing. In these and other embodiments, the routine 1100 can analyze one or more changes in depth computed by the routine 1100 at block 1105. For example, the routine 1100 can analyze changes in depth of regions corresponding to a patient's neck to determine whether a patient is straining to breathe, as discussed above with respect to FIG. 5C.

At block 1110, the routine 1100 determines whether one or more breathing abnormalities were detected at block 1109. If the routine 1100 determines that one or more breathing abnormalities were detected at block 1109, the routine 1100 can proceed to block 1111 to trigger one or more alerts and/or alarms. On the other hand, if the routine 1100 determines that one or more breathing abnormalities were not detected at block 1109, the routine 1100 can return to block 1104 to capture two or more images of one or more ROI's. In some embodiments, the routine 1100 can automatically return to block 1104 after determining whether one or more breathing abnormalities were detected at block 1109. In other embodiments, the routine 1100 can wait to return to block 1104 until instructed to do so (e.g., by a user of the system).

At block 1111, the routine 1100 triggers one or more alerts and/or alarms. In some embodiments, the routine 1100 triggers the one or more alerts and/or alarms in a manner similar to the routine 1100 at block 1102. In these and other embodiments, the routine 1100 can trigger an alert and/or alarm to indicate a concerning condition. For example, the routine 1100 can trigger an alert and/or alarm (e.g., on a user's display) to indicate a patient is exhibiting apnea. In these and other embodiments, the routine 1100 can highlight a problematic site in the ROI on a display. In these and still other embodiments, the routine 1100 can trigger different alerts and/or alarms for different breathing abnormalities. For example, the routine can trigger an alert and/or alarm for apnea and/or a different alert and/or alarm for paradoxical breathing. In other embodiments, the routine 1100 can trigger the same alert and/or alarm for all detected breathing abnormalities.

Although the steps of the routine 1100 are discussed and illustrated in a particular order, the routine 1100 in FIG. 11 is not so limited. In other embodiments, the routine 1100 can be performed in a different order. In these and other embodiments, any of the steps of the routine 1100 can be performed before, during, and/or after any of the other steps of the routine 1100. Moreover, a person of ordinary skill in the relevant art will readily recognize that the illustrated method can be altered and still remain within these and other embodiments of the present technology. For example, before, during, and/or after executing blocks 1109 and/or 1110, the routine 1100 can return to blocks 1101, 1103, 1105, and/or 1107 in addition to or in lieu of returning to block 1104. In these and other embodiments, one or more steps of the routine 1100 illustrated in FIG. 11 can be omitted and/or repeated in some embodiments.

In one aspect, a video-based patient monitoring system includes at least one processor configured to define one or more regions of interest (ROI's) on a patient and a non-contact detector having at least one image capture device. The at least one image capture device is configured to capture two or more images of the one or more ROI's. The at least one processor is further configured to: calculate a change in depth of a region of at least one of the one or more ROI's within the two or more images and assign one or more visual indicators from a predetermined visual scheme to the region of the at least one ROI based at least in part on the calculated change in depth of the region within the two or more images.

In another aspect, a method includes capturing two or more images of a patient, calculating a change in depth of regions on the patient within the two or more images; and assigning one or more visual indicators from a predetermined visual scheme to the regions based at least in part on the calculated changes in depth of the regions.

In exemplary aspects, the at least one image capture device is a depth sensing camera. In additional exemplary aspects, the at least one processor is configured to assign the one or more visual indicators to the region of the at least one ROI based at least in part on a sign and/or a magnitude of the calculated change in depth of the region within the two or more images.

In additional exemplary aspects, the one or more visual indicators include a color, a shade, a pattern, a concentration, and/or an intensity.

In additional exemplary aspects, the at least one processor is further configured to display the one or more assigned visual indicators overlaid onto to the region of the at least one ROI.

In additional exemplary aspects, the at least one processor is further configured to generate one or more breathing parameter signals for the at least one ROI, and wherein the one or more breathing parameter signals include a volume gain signal, a volume loss signal, a tidal volume signal, a minute volume signal, a respiratory rate signal, an inhalation-to-exhalation ratio, a degree of consistency signal, and/or a SpO2 signal.

In additional exemplary aspects, the at least one processor is further configured monitor one or more breathing parameter signals for the at least one ROI and to trigger an alert and/or an alarm when a volume gain signal and a volume loss signal are not approximately 180 degrees out of phase, a tidal volume signal is below a first threshold tidal volume level and/or is above a second threshold tidal volume level, and/or the tidal volume signal indicates the patient is talking and/or coughing.

In additional exemplary aspects, the at least one processor is further configured to monitor one or more breathing parameter signals for the at least one ROI and to trigger an alert and/or an alarm when a minute volume signal is below a first threshold minute volume level and/or is above a second threshold minute volume level, a respiratory rate signal is below a first threshold respiratory rate level and/or is above a second threshold respiratory rate level, an inhalation-to-exhalation ratio is below a first threshold inhalation-to-exhalation ratio value and/or is above a second threshold inhalation-to-exhalation ratio value, a degree of consistency signal is below a first threshold degree of consistency level and/or is above a second degree of consistency level, and/or a SpO2 signal is below a first threshold SpO2 level and/or is above a second threshold SpO2 level.

In additional exemplary aspects, the at least one ROI includes at least two ROI's, wherein the at least one processor is further configured to generate one or more breathing parameter signals for each ROI of the at least two ROI's, and wherein the one or more breathing parameter signals include a volume gain signal, a volume loss signal, a tidal volume signal, a minute volume signal, a respiratory rate signal, an inhalation-to-exhalation ratio, a degree of consistency signal, and/or a SpO2 signal.

In additional exemplary aspects, the at least one ROI includes at least two ROI's, and wherein the at least one processor is further configured monitor one or more breathing parameter signals generated for each ROI of the at least two ROI's and to trigger an alert and/or an alarm when a volume gain signal of a first ROI and/or a volume loss signal of the first ROI is substantially in phase with a volume loss signal of a second ROI and/or a volume gain signal of the second ROI, respectively, the volume gain signal of the first ROI, the volume loss signal of the first ROI, and/or a tidal volume signal of the first ROI is substantially out of phase with the volume gain signal of the second ROI, the volume loss signal of the second ROI, and/or a tidal volume signal of the second ROI, respectively, and/or an amplitude of the volume gain signal of the first ROI, of the volume loss signal of the first ROI, and/or of the tidal volume signal of the first ROI varies from an amplitude of the volume gain signal of the second ROI, of the volume loss signal of the second ROI, and/or of the tidal volume signal of the second ROI, respectively, by more than a predetermined threshold value.

In additional exemplary aspects, the at least one processor is further configured (i) to monitor calculated changes in depth of a region of the at least one ROI corresponding to the patient's neck and (ii) trigger an alert and/or an alarm when the at least one processor determines that the calculated changes in depth of the region corresponding the patient's neck indicate that the patient is straining to breathe.

In additional exemplary aspects, the at least one processor is further configured to identify the patient within a field of view of the at least one image capture device by performing facial recognition on the patient.

In additional exemplary aspects, the at least one processor is further configured to recognize when the patient is within a field of view of the at least one image capture device and/or to trigger an alert and/or an alarm when the at least one processor determines that the patient has fallen and/or has moved outside of the field of view.

In additional exemplary aspects, the at least one processor is further configured to display the one or more visual indicators overlaid onto the regions of the at least one ROI in real-time, display one or more generated breathing parameter signals in real-time, and/or display plots of one or more generated breathing parameter signals in real-time and over time.

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments can perform steps in a different order. Furthermore, the various embodiments described herein can also be combined to provide further embodiments.

The systems and methods described herein can be provided in the form of tangible and non-transitory machine-readable medium or media (such as a hard disk drive, hardware memory, etc.) having instructions recorded thereon for execution by a processor or computer. The set of instructions can include various commands that instruct the computer or processor to perform specific operations such as the methods and processes of the various embodiments described here. The set of instructions can be in the form of a software program or application. The computer storage media can include volatile and non-volatile media, and removable and non-removable media, for storage of information such as computer-readable instructions, data structures, program modules or other data. The computer storage media can include, but are not limited to, RAM, ROM, EPROM, EEPROM, flash memory or other solid-state memory technology, CD-ROM, DVD, or other optical storage, magnetic disk storage, or any other hardware medium which can be used to store desired information and that can be accessed by components of the system. Components of the system can communicate with each other via wired or wireless communication. The components can be separate from each other, or various combinations of components can be integrated together into a monitor or processor, or contained within a workstation with standard computer hardware (for example, processors, circuitry, logic circuits, memory, and the like). The system can include processing devices such as microprocessors, microcontrollers, integrated circuits, control units, storage media, and other hardware.

From the foregoing, it will be appreciated that specific embodiments of the technology have been described herein for purposes of illustration, but well-known structures and functions have not been shown or described in detail to avoid unnecessarily obscuring the description of the embodiments of the technology. To the extent any materials incorporated herein by reference conflict with the present disclosure, the present disclosure controls. Where the context permits, singular or plural terms can also include the plural or singular term, respectively. Moreover, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Where the context permits, singular or plural terms can also include the plural or singular term, respectively. Additionally, the terms "comprising," "including," "having" and "with" are used throughout to mean including at least the recited feature(s) such that any greater number of the same feature and/or additional types of other features are not precluded. Furthermore, as used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

What is claimed is:

1. A method of visually depicting changes in breathing of a patient, comprising:
    using a camera to detect a depth within a field of view from the camera to a torso region of a patient;
    measuring a change in the detected depth over time;
    assigning a first visual indicator from a visual scheme when a measured change in depth is positive;
    assigning a second visual indicator from the visual scheme when a measured change in depth is negative;
    assigning a third visual indicator from the visual scheme when a measured change in depth is negligible or equivalent to zero, the first and second and third visual indicators being different from each other;
    displaying on a display a video image of the patient;
    modifying the displayed video image by overlaying the assigned first or second or third visual indicator onto the torso region of the patient in the displayed video image; and
    visually depicting breathing activity of the patient in real-time by cyclically displaying the first and second visual indicators while the patient is breathing and displaying the third visual indicator while the patient is exhibiting apnea.

2. The method of claim 1, further comprising determining a respiratory rate of the patient from the measured change in depth over time.

3. The method of claim 2, further comprising triggering an alert upon determining that the respiratory rate of the patient crosses a threshold.

4. The method of claim 3, further comprising assigning a fourth visual indicator or no visual indicator to a region in the image that exhibits non-physiological or non-respiratory changes in depth.

5. The method of claim 1, wherein the first and second and third visual indicators exaggerate changes in depth detected by the camera.

6. The method of claim 1, wherein the visual scheme comprises a concentration of a pattern or a degree of an intensity or shade, wherein the concentration or the degree is positively correlated with the measured change in depth.

7. The method of claim 1, wherein overlaying the assigned first or second or third visual indicator onto the torso region of the patient in the displayed video image comprises overlaying onto a chest region of the patient at a first time and overlaying onto a back region of the patient at a second time.

8. The method of claim 1, wherein the display is remote from the camera.

9. The method of claim 1, further comprising determining a tidal volume signal from the measured change in detected depth over time, and displaying on the display a plot of the tidal volume signal, wherein the plot is displayed at the same time as the modified video image.

10. The method of claim 1, further comprising determining whether the patient is within the field of view prior to measuring the change in detected depth over time.

11. The method of claim 1, further comprising visually depicting paradoxical breathing of the patient by overlaying both the first visual indicator and the second visual indicator onto different regions of the displayed video image at the same time.

\* \* \* \* \*